United States Patent [19]
Vacher et al.

[11] Patent Number: 6,020,345
[45] Date of Patent: Feb. 1, 2000

[54] PYRIDIN-2-YL-METHYLAMINE DERIVATIVES, METHOD OF PREPARING AND APPLICATION AS MEDICINE

[75] Inventors: Bernard Vacher, Castres; Bernard Bonnaud, Lagarrigue; Wouter Koek, Viviers-les-Montagnes, all of France

[73] Assignee: Pierre Fabre Medicament, Boulogne-Billancourt, France

[21] Appl. No.: 09/308,613

[22] PCT Filed: Nov. 20, 1997

[86] PCT No.: PCT/FR97/02097

§ 371 Date: May 21, 1999

§ 102(e) Date: May 21, 1999

[87] PCT Pub. No.: WO98/22459

PCT Pub. Date: May 28, 1998

[30] Foreign Application Priority Data

Nov. 21, 1996 [FR] France .................................. 96 14217

[51] Int. Cl.[7] ...................... A61K 31/445; C07D 401/12; C07D 401/14; C07D 405/14; C07D 409/14
[52] U.S. Cl. ............................ 514/318; 546/194; 546/226
[58] Field of Search .................... 546/194, 226; 514/318

[56] References Cited

U.S. PATENT DOCUMENTS 5,286,735  2/1994  Bonnaud .................................. 514/321

FOREIGN PATENT DOCUMENTS 0538080A  4/1993  European Pat. Off. .
0661266A  7/1995  European Pat. Off. .

OTHER PUBLICATIONS

Favre H et al. Canadian Journal of Chemistry, 49(19), 3075–3085, Oct. 1971.

*Primary Examiner*—Evelyn Mei Huang
*Attorney, Agent, or Firm*—The Firm of Gordon W. Hueschen

[57] ABSTRACT

The invention concerns novel pyridin-2-yl-methylamine derivatives of formula (I):

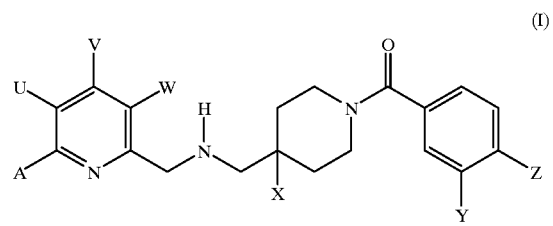

in which:
  u represents hydrogen or methyl;
  v represents hydrogen, chlorine, or methyl;
  w represents hydrogen, fluorine, or methyl;
  x represents hydrogen or fluorine;
  y represents chlorine or methyl;
  z represents hydrogen, fluorine, chlorine, or methyl;
  A represents hydrogen, fluorine, chlorine, $C_1$–$C_5$ alkyl, fluoroalkyl, cyclopropyl, a 5-membered aromatic heterocyclic group, alkoxy or alkythio, amino, cyclic amino, or alkoxycarbonyl. These compounds are useful as medicines, in particular as antidepressants or analgesics.

15 Claims, No Drawings

PYRIDIN-2-YL-METHYLAMINE DERIVATIVES, METHOD OF PREPARING AND APPLICATION AS MEDICINE

The present application is a U.S. National Application filed under 35 USC 371 of PCT/FR97/02097, filed Nov. 20, 1997 based upon French application Ser. No. 96/14217 filed Nov. 21, 1996.

Serotonin (5-hydroxytryptamine, 5-HT) is a neurotransmitter and a neuromodulator of the central nervous system which exerts its multiple physiological functions by interaction with the specific 5-HT receptors. These 5-HT receptors have been grouped into several main classes. Among these main classes, the 5-HT$_1$ class comprises receptors characterized by a high affinity for serotonin. The 5-HT$_1$ class is itself divided into a subclass of receptors whose pharmacological characteristics and regional distributions in the central nervous system are distinct.

Clinical studies of compounds having an agonist activity for the 5-HT$_{1A}$ subtype have demonstrated that the 5-HT$_{1A}$ agonists were effective in the treatment of anxiety (J. Clin. Psychiatry 1987, 48 (12 suppl.), 3–6; Int. Clin. Psychopharmacol. 1993, 8, 173–6), of depression (J. Clin. Psychopharmacol. 1990, 10 (3 suppl.), 67–76; J. Clin. Psychiatry 1991, 52, 217–20), of compulsive-obsessive disorders (Am. J. Psychiatry 1991, 148, 127–9), of panic attacks (J. Clin. Psychopharmacol. 1993, 13, 145–9), of sleeping disorders (Psychopharmacol. 1995, 117, 186–92) and of alcohol abuse (J. Clin. Psychopharmacol. 1989, 9, 379–80).

Studies in animals have demonstrated that the 5-HT$_{1A}$ agonists possess analgesic (Eur. J. Pharmacol. 1996, 295, 181–8), antiaggressive (Neurosci. Biobehav. Rev. 1994, 18, 325–38) and antiemetic (Pharmacol. Biochem. Behav. 1989, 33, 627–31; Pharmacol. Biochem. Behav. 1995, 52, 571–5) properties. The compounds having a 5-HT$_{1A}$ agonist activity have also been reported as being capable of being useful in the treatment of sexual behavior disorders (Behavioural. pharmacol. 1995, 6, 276–82), for regulating food intake (Int. Clin. Psychopharmacol. 1994, 9, 7–17) and for regulating gastric secretion (J. Pharmacol. Exp. Ther. 1995, 272, 832–7). The antihypertensive action of the 5-HT$_{1A}$ agonists, via a central mechanism, is recognized (Trends Pharm. Sci. 1990, 11, 95–6; Fundam. Clin. Pharmacol. 1993, 7, 499–511); furthermore, the 5-HT$_{1A}$ agonists have shown neuroprotective properties in models of local and global ischemia in rodents (Brain Research 1993, 630, 10–20; Arch. Int. Pharmacodyn. Ther. 1995, 329, 347–59).

Studies in vitro also tend to implicate the 5-HT$_{1A}$ receptors in the stimulation of the proliferation of lymphocytes (INPHARMA®, Aug. 26, 1995, 10; Life Sciences, 57, 2197–203).

Given the substantial therapeutic potential of compounds endowed with an agonist activity for the receptors of the 5-HT$_{1A}$ subtype, the discovery of new structures possessing 5-HT$_{1A}$ agonist properties is highly desirable. The applicant has discovered that several compounds derived from pyridin-2-yl-methylamine have an agonist activity towards the central 5-HT$_{1A}$ receptor.

The present invention therefore relates to new compounds corresponding to the general formula (I)

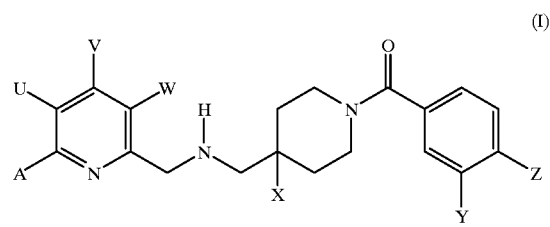

in which:
u represents a hydrogen atom or a methyl radical with the proviso that when u is a methyl radical then v and w represent a hydrogen atom;
v represents a hydrogen atom or a chlorine atom or a methyl radical with the proviso that when v represents a chlorine atom or a methyl radical then u and w represent a hydrogen atom;
w represents a hydrogen atom or a fluorine atom or a methyl radical with the proviso that when w represents a fluorine atom or a methyl radical then u and v represent a hydrogen atom;
x represents a hydrogen atom or a fluorine atom;
y represents a chlorine atom or a methyl radical;
z represents a hydrogen atom or a fluorine atom or a chlorine atom or a methyl radical;
A represents:
a hydrogen atom or a fluorine atom or a chlorine atom;
a $C_1$–$C_5$ alkyl radical, i.e. a straight or branched chain saturated aliphatic hydrocarbon radical containing 1 to 5 carbon atoms such as methyl, ethyl, propyl, butyl, pentyl, isopropyl, 1-methyl-ethyl, 1-methyl-propyl, 1-methyl-butyl, 2-methyl-propyl, 2-methyl-butyl or 3-methyl-butyl, 1-ethyl-propyl, 2-ethyl-propyl;
a fluoroalkyl radical such as monofluoromethyl (—CH$_2$F) or difluoromethyl (—CHF$_2$) or trifluoromethyl (—CF$_3$) or 1-fluoro-1-ethyl (—CHFCH$_3$) or 1,1-difluoro-1-ethyl (—CF$_2$CH$_3$);
a cyclopropyl or cyclobutyl or cyclopentyl radical;
a substituted or unsubstituted 5-membered aromatic heterocyclic group containing 1, 2, 3 or 4 heteroatoms selected from nitrogen, oxygen and sulfur without, however, more than one oxygen and/or sulfur atom being present in the heterocycle A. The aromatic heterocycles being preferably:
furan-2-yl, (O.CH:CH.CH:C—) or
furan-3-yl, (CH:CH.O.CH:C—) or
1H-pyrrol-2-yl, (NH.CH:CH.CH:C—) or
1H-pyrrol-3-yl, (CH:CH.NH.CH:C—) or
1-methyl-pyrrol-2-yl, (N(CH$_3$).CH:CH.CH:C—) or
1-methyl-pyrrol-3-yl, (CH:CH.N(CH$_3$).CH:C—) or
thiophen-2-yl, (S.CH:CH.CH:C—) or
thiophen-3-yl, (CH:CH.S.CH:C—) or
pyrazol-1-yl, (N:CH.CH:CH.N—) or
1H-pyrazol-3-yl, (CH:CH.NH.N:C—) or
1H-pyrazol-4-yl, (CH:N.NH.CH:C—) or
1-methyl-pyrazol-3-yl, (CH:CH.N(CH$_3$).N:C—) or
imidazol-1-yl, (CH:N.CH:CH.N—) or
1H-imidazol-2-yl, (NH.CH:CH.N:C—) or
1H-imidazol-4-yl, (N:CH.NH.CH:C—) or
oxazol-2-yl, (O.CH:CH.N:C—) or
oxazol-4-yl, (N:CH.O.CH:C—) or
oxazol-5-yl, (O.CH:N.CH:C—) or
isoxazol-5-yl, (O.N:CH.CH:C—) or isoxazol-4-yl, (CH:N.O.CH:C—) or
isoxazol-3-yl, (CH:CH.O.N:C—) or
thiazol-2-yl, (S.CH:CH.N:C—) or
thiazol-4-yl, (N:CH.S.CH:C—) or
thiazol-5-yl, (S.CH:N.CH:C—) or
isothiazol-5-yl, (S.N:CH.CH:C—) or
isothiazol-4-yl, (CH:N.S.CH:C—) or
isothiazol-3-yl, (CH:CH.S.N:C—) or
[1,2,4]triazol-1-yl, (CH:N.CH:N.N—) or
1H-[1,2,4]triazol-3-yl, (N:CH.NH.N:C—) or
[1,2,4]oxadiazol-3-yl, (N:CH.O.N:C—) or
[1,2,4]oxadiazol-5-yl, (O.N:CH.N:C—) or
5-methyl-[1,2,4]oxadiazol-3-yl, (N:C(CH$_3$).O.N:C—) or
1H-tetrazol-5-yl, (NH.N:N.N:C—);

an alkoxy (R$_1$O—) or alkylthio (R$_1$S—) group in which the R$_1$ radical represents:
a C$_1$–C$_5$ alkyl radical as defined above,
a monofluoromethyl or trifluoromethyl radical,
a cyclopropyl or cyclobutyl or cyclopentyl radical;
a type II amino group

(II)

in which R$_2$ and R$_3$, which are identical or different, represent hydrogen, or a C$_1$–C$_5$ alkyl radical as defined above or a cyclopropyl or cyclobutyl radical or a trifluoromethyl radical;
a type III saturated cyclic amino group

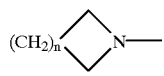

(III)

in which n may take the integers 1 or 2;
an alkoxycarbonyl group, preferably a methoxycarbonyl group (CH$_3$OCO—) or an ethoxycarbonyl group (CH$_3$CH$_2$OCO—);
as well as the addition salts of the compounds of general formula (I) with pharmaceutically acceptable inorganic acids or organic acids.

All the compounds of this invention were compared with Buspirone, 4-butyl-4-methyl-1-[4-(4-pyrimid-2-yl-piperazin-1-yl)-butyl]-piperidine-2,6-dione, sole agonist of the HTLA receptors currently commercially available, and with 8-OH-DPAT, 7-dipropylamino-5,6,7,8-tetrahydronaphthalen-1-ol which is the standard 5-HT$_{1A}$ agonist.

Like Buspirone and 8-OH-DPAT, the compounds of the invention possess a high affinity for the 5-HT$_{1A}$ receptors. However, the compounds of the invention show, in general, a selectivity in vitro which is greater than that of Buspirone and of 8-OH-DPAT in relation to the dopaminergic receptors of the D$_2$ subtype. The 5-HT$_{1A}$ versus D$_2$ selectivity is defined in the present application as being the ratio of the affinity constants (Ki) D$_2$/(Ki) 5-HT$_{1A}$. The compounds of the invention could therefore have fewer undesirable side effects than Buspirone and 8-OH-DPAT, in particular the neurological and/or endocrine disorders caused by the occupation of the receptors of the D$_2$ subtype (CNS Drugs 1996, 5 (suppl. 1), 21–35).

It has been possible to demonstrate the 5-HT$_{1A}$ agonist activity of several compounds of the invention after oral administration in rats. The 5-HT$_{1A}$ agonist activity of the compounds in question in vivo is in this case in general greater than that of Buspirone and 8-OH-DPAT. The central activity of the compounds of the invention and of the standards in rats was evaluated by their capacity to cause the retraction of the lower lip of the animal, a sensitive and specific marker for a central 5-HT$_{1A}$ agonist activity (Pharmacol. Biochem. Behav. 1989, 33, 821–27).

Several compounds of the invention therefore possess a high affinity for the 5-HT$_{1A}$ receptors in vitro and show an agonist activity on these receptors in vivo. Because of this, the compounds of the invention are considered as being capable of being useful in the treatment of the many pathologies involving serotoninergic dysfunctions such as anxiety, depression, compulsive-obsessive disorders, panic attacks, aggression, alcohol abuse, sexual disorders, sleeping disorders, perception of pain, vomiting, regulation of gastric secretion, regulation of food intake, immune diseases, vascular and cerebrovascular disorders such as high blood pressure or migraine.

The invention also relates to the addition salts and optionally the hydrates of the addition salts of the compounds of general formula (I) with pharmaceutically acceptable inorganic acids or organic acids.

The subject of the invention is also the pharmaceutical compositions containing, as active ingredient, at least one of the derivatives of general formula (I) or one of its salts or hydrates of its salts in combination with one or more pharmaceutically acceptable excipients, adjuvants or vehicles. By way of example, there may be mentioned the inclusion complexes, in particular the inclusion complexes formed by the compounds of the invention with β-cyclodextrins.

The pharmaceutical compositions according to the invention may be compositions which can be administered by the oral, nasal, sublingual, rectal or parenteral route. It is generally advantageous to formulate such pharmaceutical compositions in unit dosage form. Each dose then comprises a predetermined quantity of the active ingredient, combined with the appropriate vehicle, excipients and/or adjuvants, the quantity being calculated in order to obtain a given therapeutic effect. By way of example of a unit dosage form which can be administered by the oral route, there may be mentioned tablets, gelatin capsules, granules, powders and oral solutions or suspensions. The formulations which are appropriate for the mode of administration chosen are known and described for example in Remington, The Science and Practice of Pharmacy, 19th edition, 1995, Mack Publishing Company and can therefore be easily prepared by persons skilled in the art.

It is known that the dosage varies from one individual to another, depending on the nature and the severity of the condition, the route of administration chosen, the weight, age and sex of the patient, consequently, the effective doses will have to be determined as a function of these parameters by a specialist in this field. As a guide, the effective doses may range between 0.001 mg/kg and 100 mg/kg/day.

The compounds of general formula (I) may exist in several tautomeric forms. Such tautomeric forms, although not explicitly reported in the present application in order to simplify the graphical representation of the schemes, are nevertheless included in the field of application of the invention.

The invention finally extends to the process for the preparation of the pyridin-2-yl-methylamine derivatives of general formula (I).

The chemical process used for the preparation of the compounds of general formula (I) depends in particular on the nature of the substituents A and x.

The compounds of formula (Ia) in which:

x is a hydrogen atom or a fluorine atom;

A, u, v, w, y and z have the same meaning as above;

may be obtained by one of the two processes (a) and (b) described in scheme A.

Scheme A

According to process (a), the compound of formula (Ia) is prepared by a conventional reductive amination reaction between the aldehyde of formula (IV) and the primary amine of formula (V). The expression "a conventional reductive amination reaction" means that the aldehyde (IV) and the amine (V) are reacted in the appropriate solvent and that the mixture of the reagents (IV) and (V) is then exposed to the reducing agent according to a method well-known to persons skilled in the art. The reducing agent in question may be a simple or complex boron hydride such as, for example, sodium borohydride, potassium borohydride, sodium cyanoborohydride or sodium triacetoxyborohydride.

According to process (b), the condensation between the azido derivative of formula (VI) and the aldehyde of formula (IV) in the presence of triphenylphosphine or tri-n-butylphosphine in methanol leads to the intermediate imine of formula (VII). The imine of formula (VII) is not isolated pure but reduced in situ to the amine of formula (Ia) by means of a simple or complex boron hydride such as, for example, sodium borohydride or potassium borohydride. The term "in situ" means that the imine of formula (VII) is not subjected to any purification procedure but that the mixture of the reagents (IV), (VI) and (Ph)$_3$P or (nBu)$_3$P, in the appropriate solvent, is used directly in the reduction step.

The compounds of formula (Ib), specific cases of the compounds of formula (Ia) in which:

x is a hydrogen atom,

A, u, v, w, y and z are as defined above, may be prepared according to the method described in scheme B.

Scheme B

The condensation between the piperidin-4-yl-methylamine, which is commercially available, and the aldehyde of formula (IV) in a solvent such as benzene, toluene, cyclohexane or dichloromethane at room temperature or at the reflux temperature of the solvent with elimination of the water formed with the aid of a drying agent or by azeotropic entrainment leads to the imine of formula (VIII). The imine of formula (VIII), not isolated pure, is then acylated by means of the appropriate acid chloride, which is commercially available or which is prepared according to a conventional method from the corresponding carboxylic acid, so as to give the acylated imine of formula (IX). The acylation reaction in question is carried out in the presence of a base, generally a tertiary amine, so as to trap the hydrochloric acid released during the reaction. The acylated imine of formula (IX), which is not isolated pure, is then converted to the amine of formula (Ib) by reduction:

either in a protic solvent or a mixture of solvent of which at least one of the constituents is a protic solvent, by means of sodium borohydride, potassium borohydride or sodium cyanoborohydride;

or in an aprotic solvent by means of sodium triacetoxyborohydride.

The reaction sequence as described in scheme B may be carried out, if desired,, according to a "one-pot" technique. The term "one-pot" means that the successive steps are carried out in a single container with no manipulation other than the sequential addition of the reagents, the exchange of solvent or the addition of a cosolvent.

The compounds of formula (Ic), specific cases of the compounds of formula (Ia) in which:

u and v represent a hydrogen atom, w is a hydrogen atom or a methyl radical, x is a hydrogen atom or a fluorine atom, y and z have the same meaning as above, A is selected from:

a pyrrol-1-yl, pyrazol-1-yl, imidazol-1-yl or [1,2,4]triazol-1-yl radical, a type (II) amino group or a type (III) cyclic amino group, may be prepared according to the process summarized in scheme C.

Scheme C

The compounds of formula (Ic) may be obtained directly from the compounds of formula (Ia) in which group A is a fluorine atom or a chlorine atom by reacting with an appropriate reagent of the (HA) or (Na$^+$A$^-$) type. This process, when it is applicable, has the advantage of avoiding a protection step and a deprotection step during the preparation of the aldehyde of formula (IV). The reagent symbolized by (HA) represents a commercially available primary or secondary amine such as methylamine, ethylamine, n-propylamine, isopropylamine, isobutylamine, dimethylamine, N-ethylmethylamine, N-methylpropylamine, diethylamine, cyclobutylamine, cyclopropylamine, azetidine or pyrrolidine. The reaction between the compound of formula (Ia: A=F or Cl) and the reagent (HA) which gives the compound of formula (Ic) in which A is a type (II) amino group or a type (III) cyclic amino group is generally performed in the presence of an excess of the reagent (HA) at a temperature of between 25° C. and 150° C.

The ionized reagent (Na$^+$A$^-$) symbolizes the sodium salt of the reagent (HA) obtained after removal of a proton by means of a strong base such as for example sodium hydride. The reagents advantageously used in the ionized form (Na$^+$A$^-$) for the substitution of the fluorine or chlorine atom present in the compound (Ia: A=F or Cl) are the sodium salts of pyrrole, pyrazole, imidazole or [1,2,4]triazole. The reaction between the compounds of formula (Ia: A=F or Cl) and the reagent (Na$^+$A$^-$) which leads to the compound of formula (Ic) in which A is a pyrrol-1-yl, pyrazol-1-yl, imidazol-1-yl or [1,2,4]triazol-1-yl radical is generally carried out at a temperature of between 25° C. and 100° C. in a polar aprotic solvent.

The compounds of formula (Ia), (Ib) and (Ic) which constitute the set of compounds of formula (I) are purified according to one or more methods selected from crystallization, liquid phase chromatography techniques, extraction and filtration. They may then, if desired:

be salified by means of a pharmaceutically acceptable acid;

be used in the formation of an inclusion complex.

The preparation of the primary amines of formula (V) as well as of the azido-type derivatives of formula (VI) is detailed in scheme D.

Scheme D

The epoxide of formula (XI) is obtained from the acylated piperidone of formula (X) according to a method similar to the method described by Popp (J. Heterocyclic Chem. 1978, 15, 675–76).

The epoxide of formula (XI), when treated with an excess of the hydrogen fluoride-pyridine complex, leads regioselectively to the fluorohydrin of formula (XII) (Synthesis 1994, 225–38). The primary alcohol function of the fluorohydrin of formula (XII) is then activated in the form of a sulfonic acid ester to give the compound of formula (XIII) in which "LG" symbolizes a 4-methylphenylsulfonyloxy, methanesulfonyloxy or trifluoromethanesulfonyloxy group.

According to route (c), the reaction of the derivative of formula (XIII) with potassium phthalimide gives the compound of formula (XIV) which, upon treatment by means of an excess of hydrazine hydrate, ethylenediamine or ethanolamine, leads to the primary amine of formula (V).

According to route (d), the reaction of the derivative of formula (XIII) with an alkali metal azide such as for example sodium or lithium azide gives the compound of formula (VI), which may in turn:

either be used in a Staudinger-aza-Wittig-type condensation as described above, scheme A process (b);

or be converted to the primary amine of formula (V) by reduction of the azido function by means of a metallic salt such as for example stannous chloride in a protic solvent or a mixture of protic solvents, route (e).

The process for the preparation of the aldehydes of formula (IV) depends on the nature of the group A and on the nature of the substituents u, v and w.

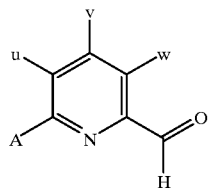

IV

The aldehyde of formula (IVa) in which:
the substituents u, v and w represent a hydrogen atom,
the group A is a fluorine atom,
may be obtained by the process described in scheme E.
Scheme E The aldehyde of formula (IVa) is prepared by an oxidative cleavage of the enamine of formula (XV) by means of sodium periodate according to an experimental protocol similar to that described by Coe (Tetrahedron Lett. 1994, 35, 219–22). The enamine of formula (XV), which is in general not isolated pure, may itself be prepared from 2-fluoro-6-methylpyridine, which is commercially available, according to a method similar to that described by Bredereck (Chem. Ber. 1968, 101, 4048–56).

The method for preparing the aldehyde of formula (IVb) in which:
the substituents u, v and w represent a hydrogen atom,
the group A is a chlorine atom, is described in Chem. Pharm. Bull. 1990, 38, 2446–58.

The aldehydes of formula (IVc) in which:
the substituents u, v and w represent a hydrogen atom;
the group A represents:
an alkoxy group ($R_1O$—) or an alkylthio group ($R_1S$—) in which $R_1$ is as defined above,
a type (II) amino group ($R_2R_3N$—) in which $R_2$ and $R_3$, which are identical or different, are as defined above;
a type (III) cyclic amino group, preferably an azetidin-1-yl radical;
may be prepared according to the process described in scheme F.
Scheme F The aldehyde function in the compound of formula (IVa) is first protected in the form of a [1,3]dioxolan-2-yl group under operating conditions similar to those used for the formation of 2-[1,3]dioxolan-2-yl-pyridine from 2-pyridinecarbaldehyde (J. Heterocyclic Chem. 1987, 24, 623–28). The substitution of the fluorine atom present in the compound of formula (XVI) by means of the appropriate reagent (HA) or ($Na^+A^-$) then makes it possible to introduce the desired A group. The reagent symbolized by (HA) represents a primary or secondary amine of the mono- or di($C_1$–$C_5$alkyl)amine type or a cyclic amine such as azetidine or pyrrolidine. The reaction between the acetal of formula (XVI) and the reagent (HA) which gives the compound of formula (XVII) in which A is an amino group of the mono- or di($C_1$–$C_5$alkyl)amino type or an azetidin-1-yl radical or a pyrrolidin-1-yl radical is performed in the presence of an excess of the reagent (HA) at a temperature of 100° C. in a polar solvent.

The ionized reagent ($Na^+A^-$) symbolizes a sodium thiolate or alcoholate obtained by deprotonation of the corresponding thiol or alcohol by means of a strong base. The reaction between the acetal of formula (XVII) and the reagent ($Na^+A^-$) which gives the compound of formula (XVII) in which A represents a group of the ($C_1$–$C_5$)alkoxy or ($C_1$–$C_5$)alkylthio type is carried out at a temperature of between 25° C. and 100° C. in a polar solvent. The aldehyde function present in the compound of formula (IVc) is then regenerated by acid hydrolysis of the acetal function of the compound of formula (XVII) by means of an aqueous solution of formic acid at a temperature of between 20° C. and 60° C.

The aldehydes of formula (IVd) in which:
the substituents u, v and w represent a hydrogen atom,
the group A is either a furan-2-yl radical or a furan-3-yl radical,
may be obtained according to the process described in scheme G.
Scheme G Patent JP 05255251 describes the preparation of trifluoromethanesulfonic acid 6-methylpyridin-2-yl ester of formula (XXIV) from 6-methylpyridin-2-ylamine. In the present application, the compound (XXIV) was obtained by reacting an appropriate derivative of trifluoromethanesulfonic acid with 6-methylpyridin-2-ol, which is commercially available.

The derivative of formula (XXIV) may then be coupled with the organozinc compounds derived from 2-lithiofuran or 3-lithiofuran, in the presence of an appropriate palladium catalyst, so as to give respectively 2-furan-2-yl-6-methylpyridine or 2-furan-3-yl-6-methylpyridine of formula (XXV). The 2-lithiofuran and 3-lithiofuran were obtained according to the methods described in J. Heterocyclic Chem. 1975, 195–96. The N-oxide intermediate of formula (XXVI) is then prepared by treating the compound of formula (XXV) by means of an organic peroxide such as for example 3-chloroperoxybenzoic acid in a halogenated solvent such as for example dichloromethane or chloroform.

The reaction between the N-oxide derivative of formula (XXVI) and trifluoroacetic anhydride, according to the method described by Matsumoto (Heterocycles, 1986, 24, 2169–72) gives, as an intermediate, the trifluoroacetic acid 6-furan-2-yl-pyridin-2-yl-methyl ester or the trifluoroacetic acid 6-furan-3-yl-pyridin-2-yl-methyl ester which is not isolated pure but saponified in situ by means of an aqueous solution of an inorganic base to give the compound of formula (XXVII).

The reaction solvent for the original Matsumoto experimental protocol (N,N-dimethylformamide) may advantageously be replaced with an anhydrous ether solvent such as for example 1,4-dioxane or tetrahydrofuran. The oxidation of the alcohol of formula (XXVII) to the aldehyde of formula (IVd) may be carried out by means of manganese dioxide or of an activated derivative of dimethyl sulfoxide such as for example dimethyl sulfoxide activated by the sulfur trioxide-pyridine complex or by oxalyl chloride, according to techniques well known to persons skilled in the art.

The derivative of formula (IVd) in which the group A is either a furan-2-yl radical or a furan-3-yl radical may also be obtained according to the chemical process used for the preparation of the aldehydes of formula (IVe) in which:

the substituents u and v represent a hydrogen atom or a methyl radical, the substituent w is a hydrogen atom or a fluorine atom or a methyl radical without, however, more than one methyl radical being simultaneously present at positions 3, 4 and 5 of the pyridine ring and when w is a fluorine atom, then u and v are hydrogen atoms, the group A is selected from a furan-2-yl or furan-3-yl or thiophen-2-yl or pyrrol-2-yl or 1-methyl-pyrrol-2-yl radical.

The process used for the preparation of the aldehydes of formula (IVe) is summarized in scheme H.

All the primary alcohols of formula (LVII), starting compounds used in the process summarized in scheme H are compounds which are known or which are prepared according to conventional methods:

(6-chloropyridin-2-yl)methanol (LVIIa) is a compound whose method of preparation is described in the chemical literature (Tetrahedron 1982, 38, 3277–80);

(5-methyl-6-chloropyridin-2-yl)methanol (LVIIb) is obtained by reducing 5-methyl-6-chloropyridine-2-carboxylic acid ethyl ester by means of sodium borohydride in ethanol, itself prepared according to the method described by Hoornaert (Tetrahedron 1996, 52, 2591–2602);

(3-methyl-6-chloropyridin-2-yl)methanol (LVIIc) is obtained by reducing 3-methyl-6-chloropyridine-2-carbaldehyde by means of sodium borohydride in methanol, itself prepared by methylation of 6-chloropyridine-2-carbaldehyde (IVb) according to the method described by Comins (J. Org. Chem. 1990, 55, 69–73);

(4-methyl-6-bromopyridin-2-yl)methanol (LVIId) is obtained from 2-bromo-4,6-dimethylpyridine by the modified Matsumoto method. The preparation of 2-bromo-4,6-dimethylpyridine is carried out from commercially available 2-amino-4,6-dimethylpyridine according to a process similar to that described by Adams (J. Amer. Chem. Soc. 1954, 76, 3168–71).

Scheme H

The primary alcohol function of the compound of formula (LVII) is first protected, for example in the form of a trimethylsilanyl-ethoxymethyl group, abbreviated SEM, according to an experimental protocol well known to persons skilled in the art. When the substituent at the 6-position is a bromine atom, the compound of formula (XXVIIIb) may be used directly in the next stage. When the substituent at the 6-position is a chlorine atom, the compound (XXVIIIa) is first converted to the intermediate (XXXI) before being used in the next step. The compound of formula (XXX), an intermediate in the preparation of the triflate of formula (XXXI), is obtained by applying a method similar to that described by Sieburth (J. Amer. Chem. Soc. 1991, 113, 8163–64).

The coupling of the derivatives of formula (XXXI) or (XXVIIIb) with the boronic acids or esters or the stannanes derived from the desired aromatic heterocycles, symbolized by (AM), in the presence of an appropriate palladium catalyst according to the conventional Suzuki or Stille methods, gives the compound of formula (XXXII).

In the case where the boronic acids or the stannanes of the desired aromatic heterocycles (AM) are not commercially available, they were prepared by transmetallation of the corresponding lithium-containing heterocycles, which are themselves obtained according to experimental protocols well known to persons skilled in the art. The cleavage of the trimethylsilanyl-ethoxymethyl group by means of tetrabutylammonium fluoride according to the method described in Tetrahedron Lett. 1988, 29, 5417–18 gives the primary alcohol of formula (XXXIII) which is oxidized to the aldehyde of formula (IVe) under experimental conditions identical to those described above for the oxidation of (XXVII) to the aldehyde (IVd).

The aldehydes of formula (IVf), (IVg) and (IVh) described below are all derived from a common precursor 2-[1,3]dioxolan-2-yl-pyridine-2-carbonitrile of formula (XXXVI) whose method of preparation is summarized in scheme I.

Scheme I

The N-oxide intermediate of formula (XXXV) obtained by oxidation of the derivative of formula (XXXIV) by means of an organic peroxide, treated under conditions similar to those described by Fife (J. Org. Chem. 1983, 48, 1375–77), gives the compound of formula (XXXVI).

The aldehydes of formulae (IVf) in which:

the substituents u, v and w represent a hydrogen atom;

the group A represents a 1H-imidazol-2-yl or thiazol-2-yl or oxazol-2-yl radical;

are prepared according to the process summarized in scheme J, route f.

Scheme J, route f

The derivative of formula (XXXVII), is obtained by addition of methanol to the compound of formula (XXXVI). The condensation of a bifunctional derivative such as ethylenediamine, 2-aminoethanethiol or 2-aminoethanol or of their hydrochlorides with the derivative of formula (XXXVII) gives the compounds of formula (XXXVIII) in which Q represents either an NH group or a sulfur atom or an oxygen atom.

The condensation reaction in question is carried out by heating the compound of formula (XXXVII) and the desired bifunctional reagent in the absence of solvent or at the reflux temperature of an alcoholic solvent. The oxidation of the derivatives of formula (XXXVIII) by means of manganese dioxide, of nickel peroxide or of barium permanganate gives the compounds of formula (XXXIX). The oxidation reaction in question is carried out in general at the reflux temperature of an inert apolar solvent, optionally removing the water formed during the reaction by one of the conventional techniques well known to persons skilled in the art. The acid hydrolysis of the acetal of formula (XXXIX) under conditions similar to those used for the hydrolysis of the acetal of formula (XVII) gives the aldehyde (IVf).

The aldehydes of formula (IVg) in which:

the substituents u, v and w represent a hydrogen atom, the group A represents an oxadiazol-3-yl or methyl-5-oxadiazol-3-yl radical, are obtained according to the process summarized in scheme J, route g.

Scheme J, route g

The addition of hydroxylamine hydrochloride to the compound of formula (XXXVI) gives the compound of formula (XXXX). The condensation of an appropriate derivative of acetic acid such as acetyl chloride with the intermediate of formula (XXXX) gives the derivative of formula (XXXXI) in which $R_4$ is a methyl radical.

In a similar manner, the condensation of an appropriate derivative of formic acid such as an alkyl orthoformate with the compound of formula (XXXX) gives the derivative of formula (XXXXI) in which $R_4$ is a hydrogen atom. The aldehyde of formula (IVg) is then obtained by hydrolysis of the [1,3]dioxolan-2-yl function of the compound of formula (XXXXI) under conditions similar to those used for the hydrolysis of the acetal (XVII) to the aldehyde (IVc).

The aldehydes of formula (IVh) in which:

the substituent u is a hydrogen atom or a methyl radical, the substituents v and w represent a hydrogen atom, the group A represents a 1H-pyrazol-3-yl or 1-methyl-1-pyrazol-3-yl radical, may be obtained according to the process described in scheme J, route h.

Scheme J, route h

The addition of methylmagnesium bromide or chloride to the compound of formula (XXXVI) gives the derivative of formula (XXXXII). The compound of formula (XXXXIII) is then prepared by condensation of N,N-dimethylformamide dimethyl acetal or of an equivalent reagent such as for example tert-butoxy-bis(dimethylamino) methane or tris(dimethylamino)methane with the ketone of formula (XXXXII). The condensation reaction in question is carried out in an anhydrous solvent such as for example tetrahydrofuran or N,N-dimethylformamide. The reaction of the hydrazine hydrate with the intermediate of formula (XXXXIII) according to methods well known to persons skilled in the art then gives the compound of formula (XXXXIV).

According to route (i), the acid hydrolysis of the acetal of formula (XXXXIV) under conditions similar to those used above gives the aldehyde of formula (IVh-1).

According to route (j), the compound of formula (XXXXIV) is first regioselectively methylated by means of methyl iodide in a basic medium and then the acetal function hydrolyzed to the aldehyde (IVh-2) under conditions similar to those used for the hydrolysis of the acetal of formula (XVII) to the aldehyde (IVc).

The aldehyde of formula (IVi) in which:

the substituents u, v and w represent a hydrogen atom, the group A represents an isopropyl radical, is described in patent WO 93/21158 where it was prepared by methylation of 6-ethylpyridine-2-carbaldehyde. In the present application, the aldehyde of formula (IVi) was advantageously obtained according to the process summarized in scheme K.

Scheme K

The unsaturated derivative of formula (XXXXV) may be prepared by a conventional Wittig reaction between 1-(6-[1,3]dioxolan-2-yl-pyridin-2-yl)ethanone of formula (XXXXII) and the anion derived from (methyl)triphenylphosphonium bromide, itself obtained by treating (methyl)triphenylphosphonium bromide by means of potassium tert-butoxide. The reduction of the double bond of the 2-[1,3]dioxolan-2-yl-6-isopropenyl-pyridine of formula (XXXXV) at a low hydrogen pressure in the presence of an appropriate catalyst such as for example palladium on carbon gives the 2-[1,3]dioxolan- 2-yl-6-isopropylpyridine of formula (XXXXVI). The hydrolysis of the acetal of formula (XXXXVI) under conditions similar to the conditions used above for the hydrolysis of the acetal of formula (XVII) to the aldehyde (IVc) gives the aldehyde (IVi).

The aldehydes of formula (IVj) in which:

the substituents u, v and w represent a hydrogen atom, the group A represents a 1-fluoro-1-ethyl group, may be prepared by the process described in scheme L.

Scheme L

The reduction of the ketone function of the compound of formula (XXXXII), which is carried out by means of sodium borohydride in methanol at room temperature, gives the secondary alcohol of formula (XXXXVII). The fluorinated acetal of formula (XXXXVIII) is then prepared by treating the alcohol of formula (XXXXVII) by means of diethylamine trifluorosulfide, abbreviated DAST, according to a conventional method known to persons skilled in the art. The aldehyde (IVj) is obtained by acid hydrolysis of the acetal function of the compound of formula (XXXXVIII) under conditions identical to those described above for the hydrolysis of the acetal (XVII) to the aldehyde (IVc).

The aldehyde of formula (IVk) in which:

the substituents u, v and w represent a hydrogen atom, the group A represents an oxazol-5-yl radical, may be obtained according to the method described in scheme M.

Scheme M

The method for preparing the 6-[1,3]dioxolan-2-yl-pyridine-2-carbaldehyde of formula (XXXXIX) is described in the chemical literature (Monatsh. Chem. 1993, 124, 881–91). The condensation of tosylmethylisocyanate, abbreviated TOSMIC, with the derivative of formula (XXXXIX), according to an experimental protocol similar to that reported in Tetrahedron Lett. 1972, 2369–72, gives the acetal of formula (L). The aldehyde (IVk) is then obtained by hydrolysis of the acetal function of the compound of formula (L) under operating conditions similar to those described above for the hydrolysis of the acetal (XVII) to the aldehyde (Ivc).

The aldehyde of formula (IVl) in which:

the substituents u, v and w represent a hydrogen atom, the group A represents a cyclopropyl radical, may be prepared by the process described in scheme N.

Scheme N

The intermediate of formula (LI) is obtained by a wittig reaction between the aldehyde of formula (XXXXIX) and (methyl)triphenylphosphonium bromide in the presence of a base such as for example potassium carbonate. The cyclopropane derivative of formula (LII) is then prepared by addition of the anion derived from trimethylsulfonium iodide to 2-[1,3]dioxolan-2-yl-6-ethenyl-pyridine (LI) according to a method similar to the method described in J. Org. Chem. 1973, 38, 3942–44. The deprotonation of the trimethylsulfonium iodide is carried out by means of n-butyllithium in tetrahydrofuran. The aldehyde of formula (IVl) is then obtained from the derivative of formula (LII) under operating conditions similar to the conditions used above for hydrolysis of acetal of formula (XVII) to the aldehyde (IVc).

The aldehydes of formula (IVm) in which:

the substituents u, v and w represent a hydrogen atom, the group A represents either a monofluoromethyl group or a difluoromethyl group, are obtained by the process described in scheme O.

Scheme O

According to route (k), (6-[1,3]dioxolan-2-yl-pyridin-2-yl)methanol (LIII), a precursor of the aldehyde of formula (XXXXIX), treated with diethylamine trifluorosulfide (DAST) in a halogenated solvent gives the fluorinated acetal of formula (LIV). The derivative of formula (LIV) is then converted to the aldehyde of formula (IVm-1) under conditions similar to those used above for the hydrolysis of the acetal (XVII) to the aldehyde(IVc).

According to route (1), the aldehyde of formula (XXXXIX) treated with diethylamine trifluorosulfide (DAST) gives the difluorinated acetal of formula (LV). The difluorinated acetal of formula (LV) is then converted to the aldehyde of formula (IVm-2) under experimental conditions similar to those described above, (route k)

The aldehyde of formula (IVo) in which:

the substituents u, v and w represent a hydrogen atom, the group A represents a methoxycarbonyl group, is obtained by the method described in scheme P.

Scheme P

The 6-hydroxymethylpyridine-2-carboxylic acid methyl ester of formula (LVI) is prepared from 2,6-pyridinecarboxylic acid methyl ester according to the protocol described in Z. Naturforsh, 1994, 49b, 1127–36. The oxidation of the alcohol of formula (LVI) under experimental conditions similar to those described for the oxidation of the alcohol of formula (XXVII) to the aldehyde (IVd) then gives the aldehyde of formula (IVo).

The methods for preparing the aldehyde of formula (IVp) in which:

the substituents A, u and w represent a hydrogen atom, the group v is a chlorine atom, and the aldehyde (IVr) in which:

the substituents A, v and w represent a hydrogen atom, the group u is a methyl radical, are described in Arch. Pharm. (Weinheim Ger.) 1977, 310, 128–36.

The aldehyde of formula (IVq) in which:

the substituents A, u and v represent a hydrogen atom, the group w represents a fluorine atom, is a known compound whose preparation is described in Tetrahedron 1983, 39, 2009–21.

The aldehydes of formula (IVs) in which:

the substituents u, v and w represent a hydrogen atom or a methyl radical without, however, more than one methyl radical being simultaneously present at positions 3, 4 and 5 of the pyridine ring, the group A is a type (II) amino group ($R_2R_3N$—) in which $R_2$ and $R_3$ are as defined above or a type (III) cyclic amino group, are prepared by processes described in scheme Q.

Scheme Q

The primary alcohols of formula (LVII) whose methods of preparation are given in the descriptive part of scheme H are reacted with a primary or secondary amine of the mono- or di($C_1$–$C_5$alkyl)amine type, preferably methylamine or dimethylamine, or a type (III) cyclic amine, preferably azetidine, to give the compound of formula (LVIII). This reaction is generally performed at a temperature of between 70° C. and 120° C. in a polar solvent. The oxidation of the primary alcohol function of the compound of formula (LIX) to the aldehyde of formula (IVs) is then carried out by means of activated manganese dioxide at the reflux temperature of a halogenated solvent such as for example chloroform.

The compounds of formula (IVa), (IVb), (IVc), (IVd), (IVe), (IVf), (IVg), (IVh), (IVi), (IVj), (IVk), (IVl), (IVm), (IVn), (IVo), (IVp), (IVq), (IVr) and (IVs) constitute the set of compounds of formula (IV).

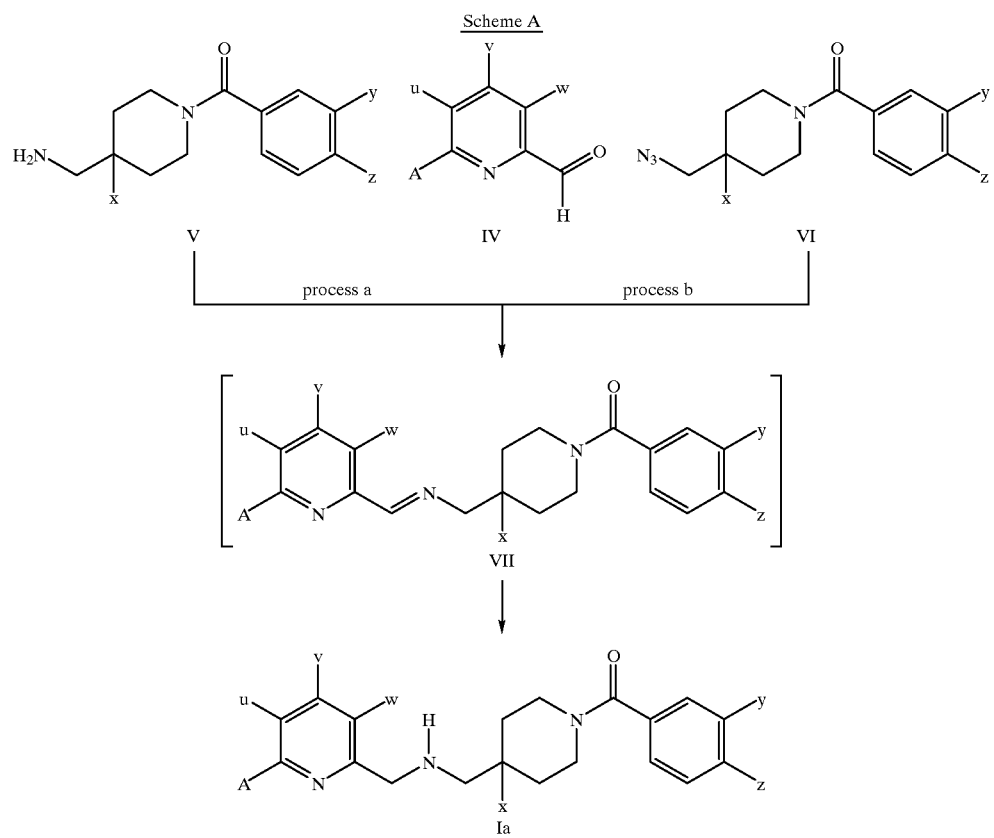

Scheme A

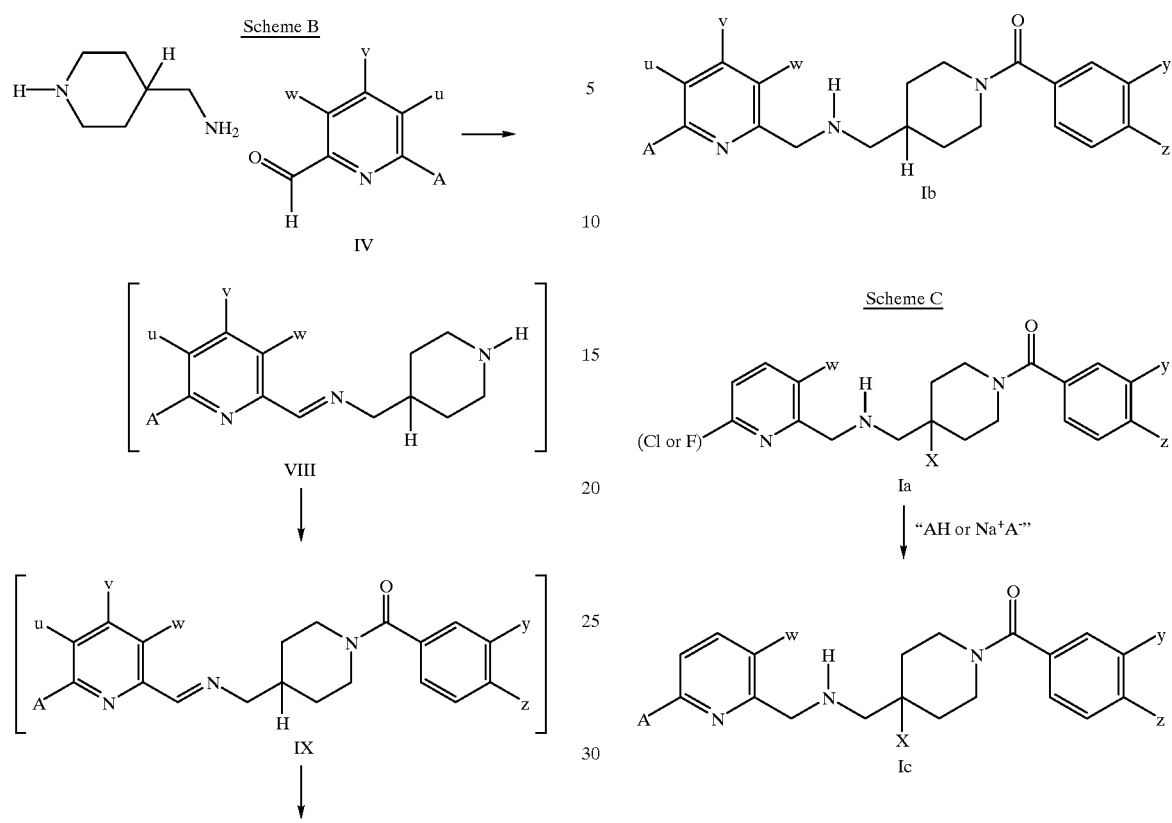
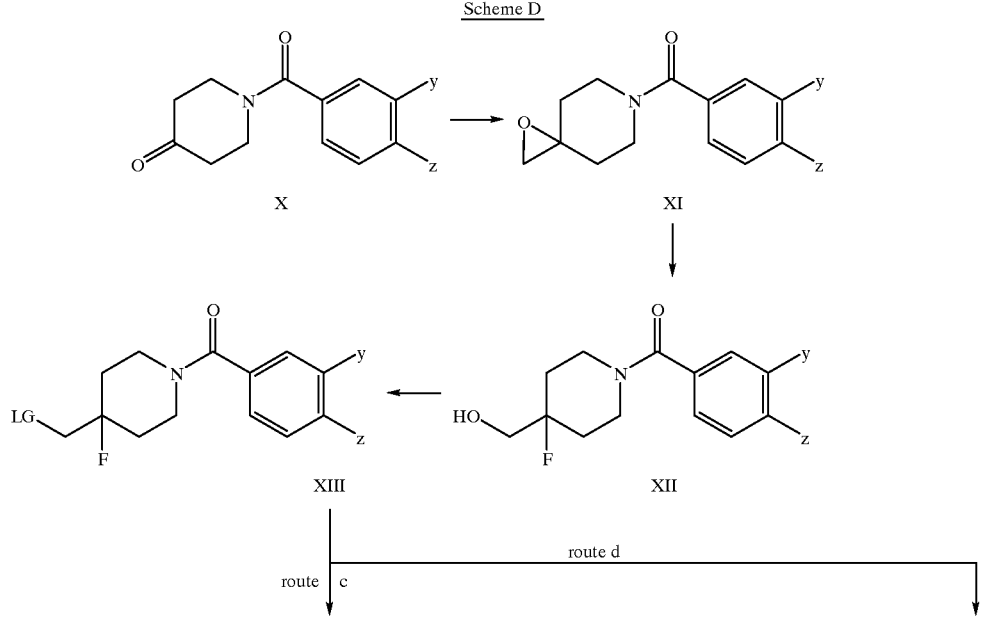

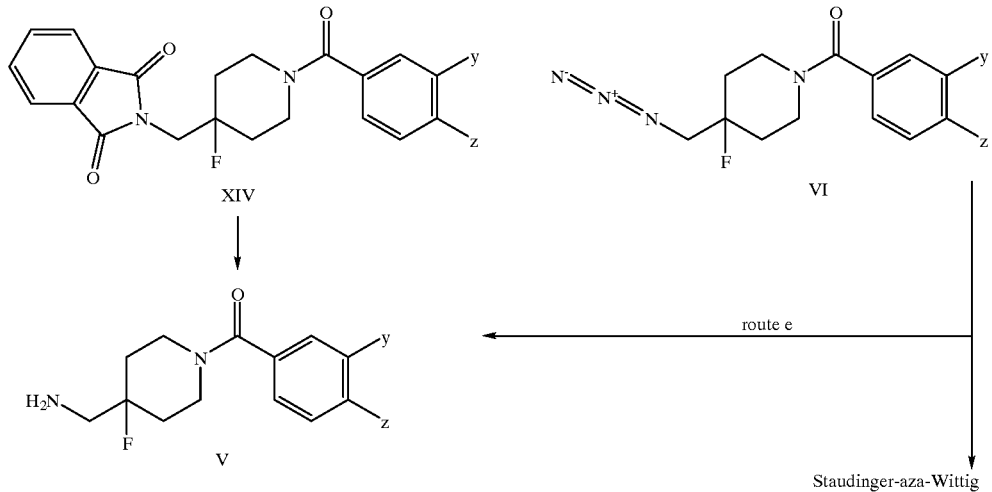
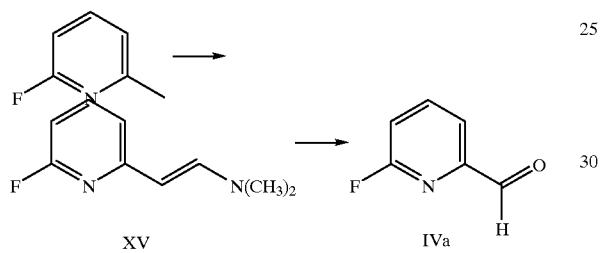
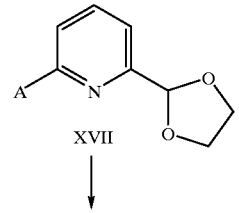
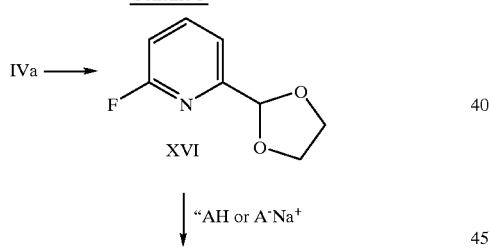
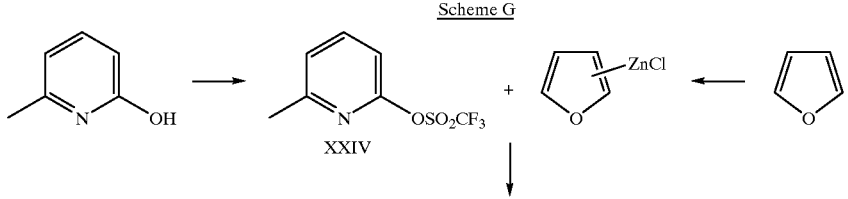

-continued
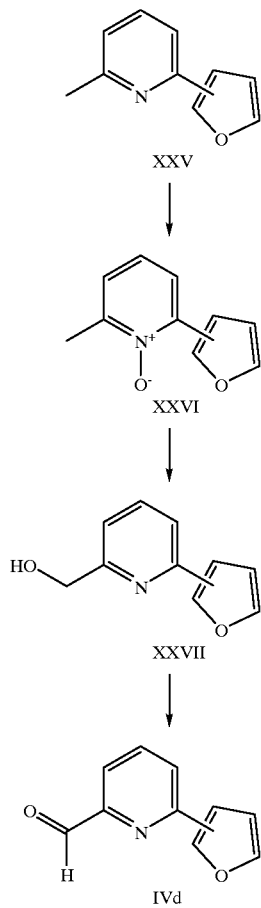
Scheme H
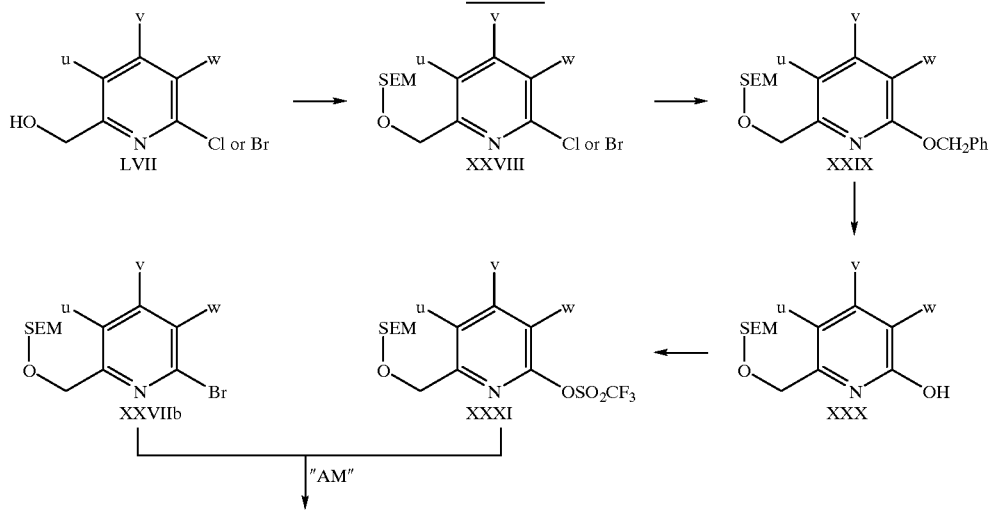

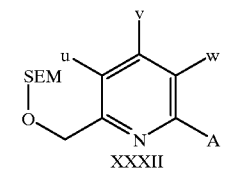
XXXII
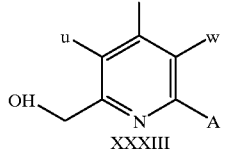
XXXIII
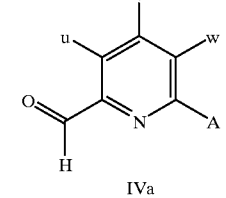
IVa
Scheme I
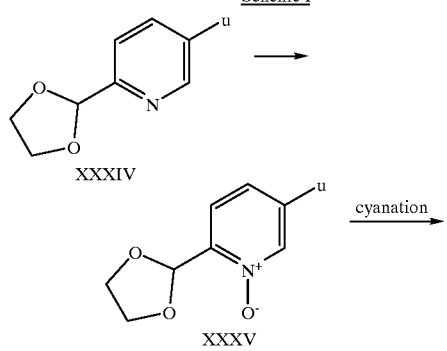
cyanation
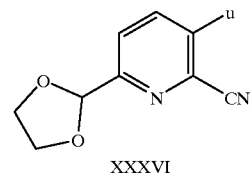
XXXVI
Scheme J
XXXVI
route f route g route h
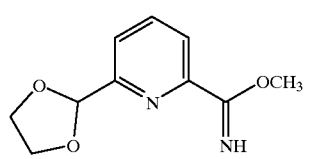
XXXVII
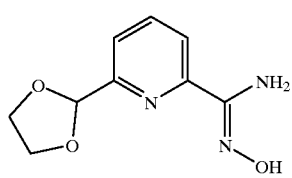
XXXX
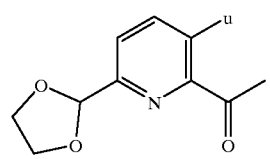
XXXXII

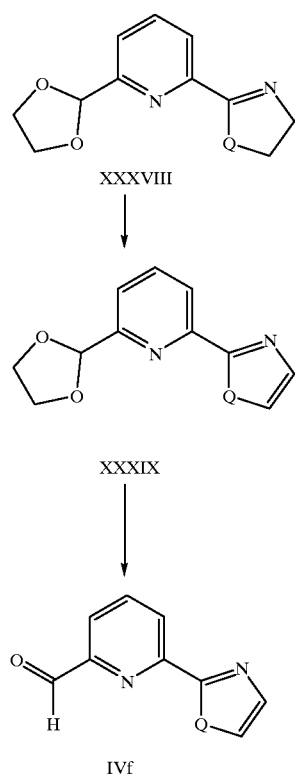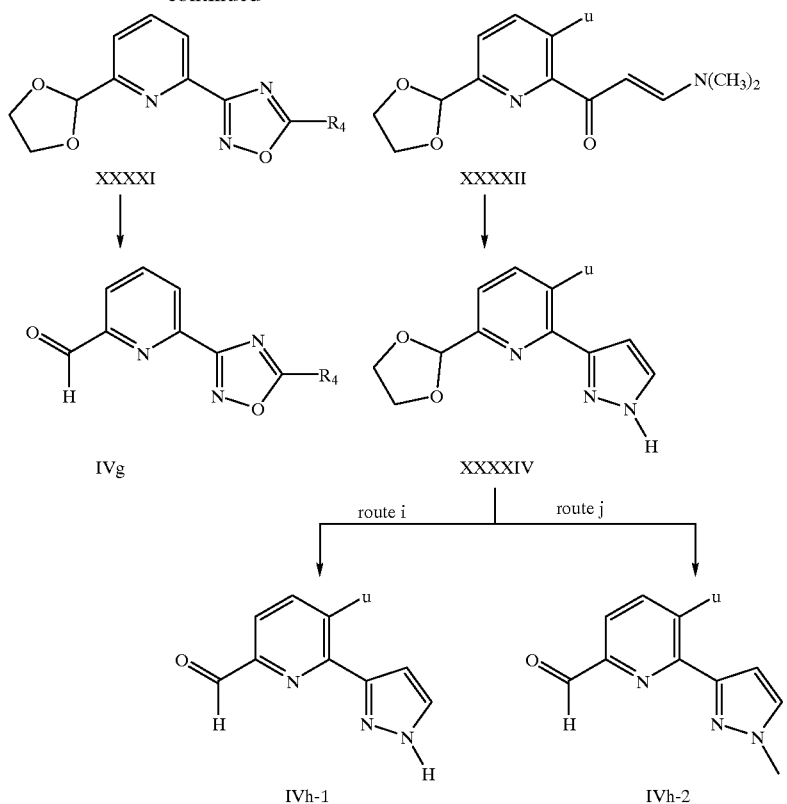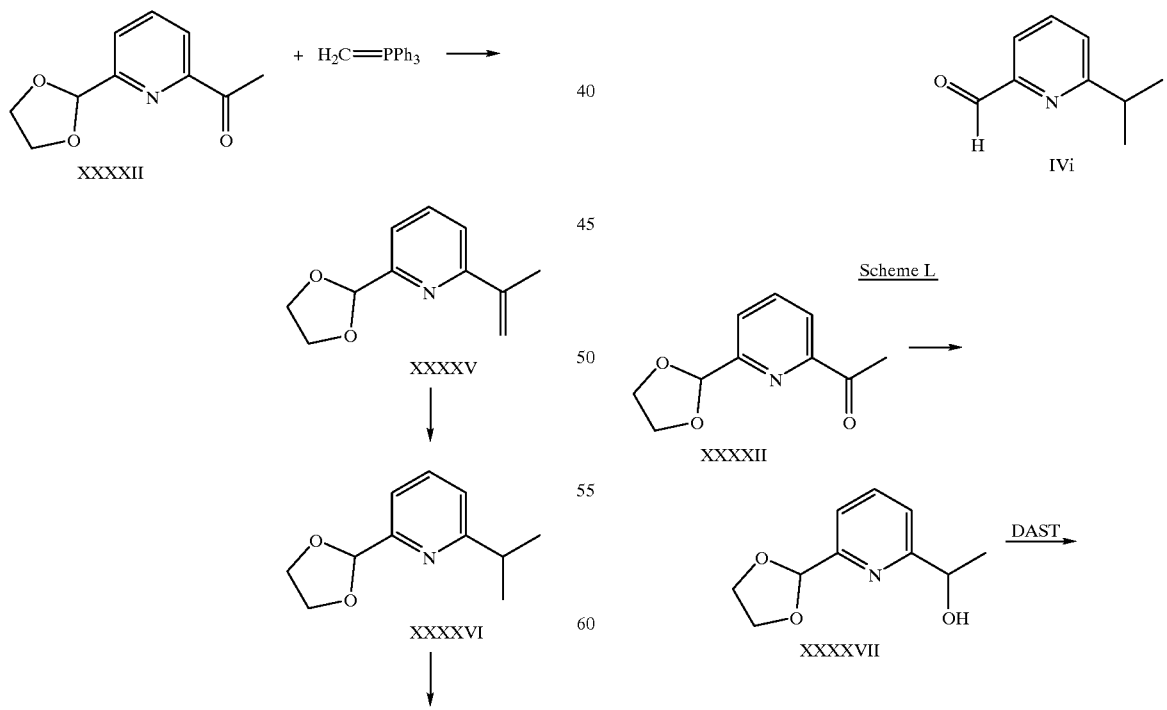

-continued
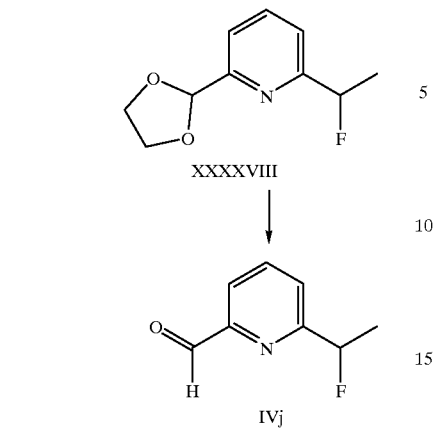
XXXXVIII
IVj
Scheme M
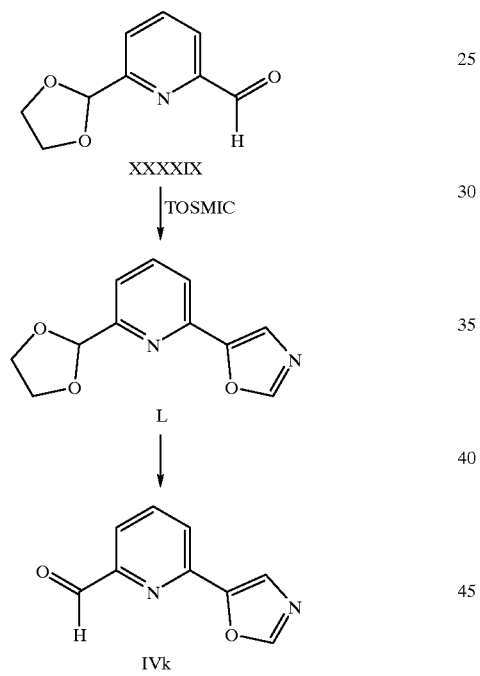
XXXXIX
TOSMIC
L
IVk
-continued
Scheme N
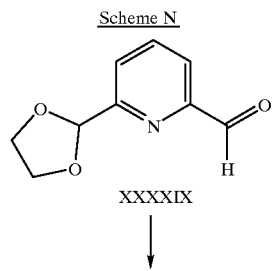
XXXXIX
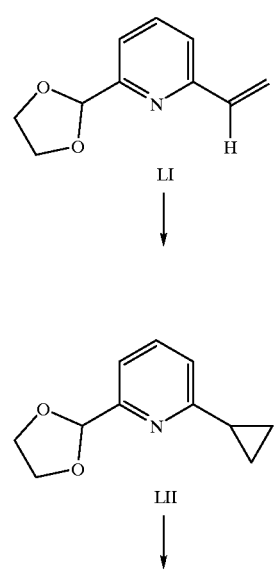
LI
LII
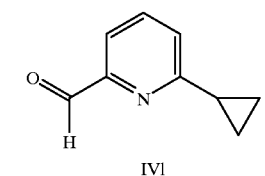
IVl

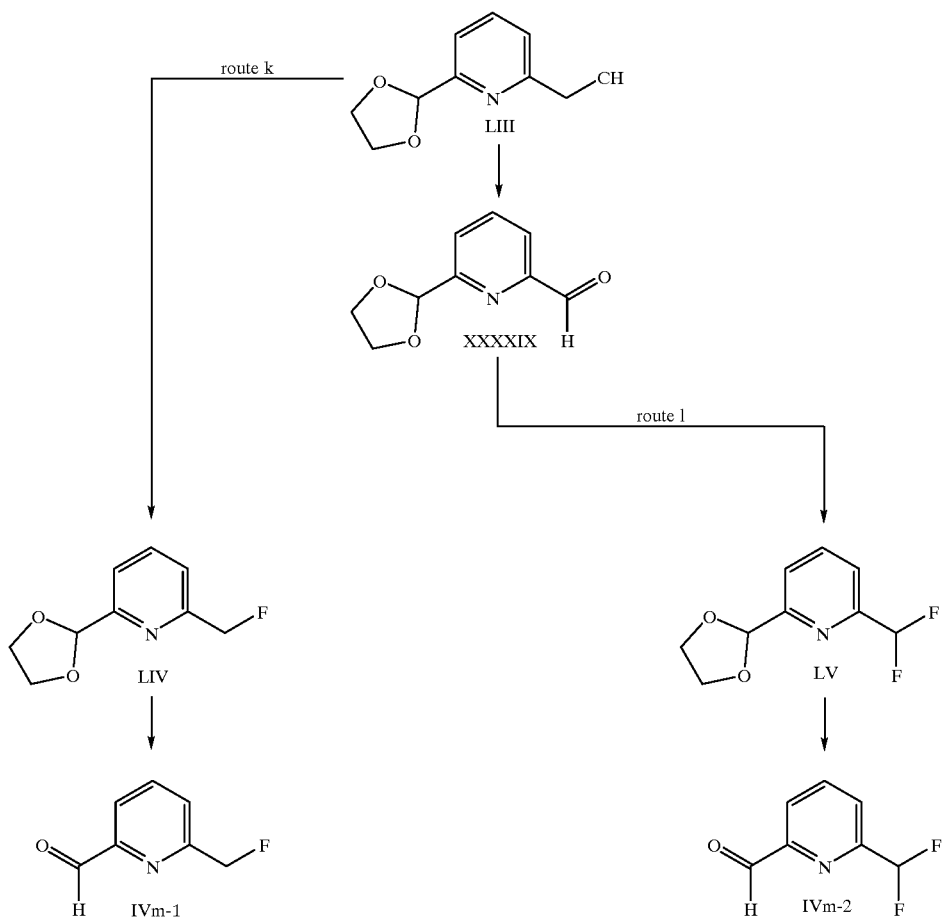
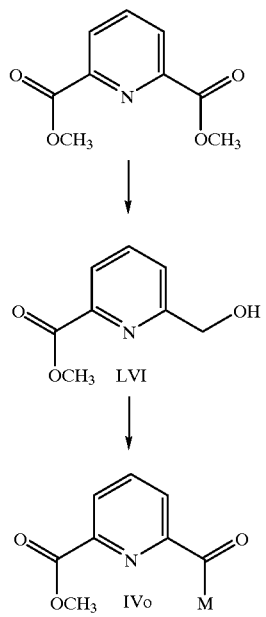
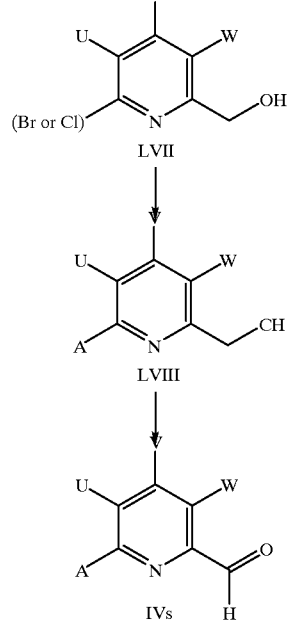

The following examples illustrate the invention and do not limit it in any manner.

In the examples below:

(i) The progress of the reactions is monitored by thin-layer chromatography (TLC) and consequently the reaction times are stated only as a guide.

(ii) Various crystalline forms may give different melting points, the melting points reported in the present application are those for the products prepared according to the method described and are not corrected.

(iii) The structure of the products obtained according to the invention is confirmed by nuclear magnetic resonance (NMR) spectrum, infrared (IR) spectrum and percentage analysis, the purity of the final products is checked by TLC.

(iv) The NMR spectra are recorded in the appropriate solvent. The chemical shifts (δ) are expressed in parts per million (ppm) relative to tetra-methylsilane. The multiplicity of the signals is indicated by: s, singlet; d, doublet; t, triplet; q, quadruplet; m, multiplet; b, broad.

(v) The various symbols for the units have their usual meaning: mg (milligram); g (gram); kg (kilogram); ml (milliliter); °C. (degrees Celsius); mmol (millimole); nmol (nanomole); cm (centimeter); μm (micrometer). The abbreviations have the following meaning: m.p. (melting point); b.p. (boiling point).

(vi) "Room temperature" is understood to mean a temperature of between 20° C. and 25° C.

In the present application, the pressure values are given in millibar.

EXAMPLE 1

Preparation of 6-fluoropyridine-2-carbaldehyde (IVa)

30 g of 2-fluoro-6-methylpyridine (270 mmol) and 70 g of tert-butoxybis(dimethylamino)methane (405 mmol) are mixed under a nitrogen atmosphere. The mixture is heated at 140° C. for 24 hours. The mixture is diluted with 50 ml of tetrahydrofuran and the solution obtained is added dropwise to an aqueous solution of 115 g of sodium periodate (538 mmol). The mixture is stirred overnight at room temperature, the precipitate formed is removed by filtration and then the tetrahydrofuran is evaporated off. The residue is extracted with dichloromethane, the organic phase is dried over magnesium sulfate, filtered and then the solvent is evaporated under vacuum. The title product is isolated by distillation in a bulb oven, b.p.$_{77}$: 70–80° C. 34 g of a yellow oil containing about 20% of N,N-dimethylformamide are recovered.

$^1$H NMR (CDCl$_3$) δ: 7.16 (dd, 1H); 7.82 (dd, 1H); 7.96 (m, 1H); 9.90 (s, 1H).

IR (film) σ: 1713 cm$^{-1}$ (C=O).

EXAMPLE 2

Preparation of 6-dimethylaminopyridine-2-carbaldehyde (IVc-1)

Stage 1: (6-[1,3]dioxolan-2-yl-pyridin-2-yl)dimethyl-amine 0.60 g of 2-[1,3]dioxolan-2-yl-6-fluoropyridine (3.55 mmol) and 2.50 ml of dimethylamine at 33% in ethanol (17.7 mmol) are mixed and then the mixture is heated at the temperature of 100° C. for 12 hours. After evaporation under vacuum, the residue is taken up in chloroform, the mixture is washed with water, dried over magnesium sulfate, filtered and the chloroform is evaporated under vacuum. The title product is obtained in the form of a yellow oil which is used in the next stage without further purification.

$^1$H NMR (CDCl$_3$) δ: 3.07 (s, 6H); 4.10 (m, 4H); 5.72 (s, 1H); 6.46 (d, 1H); 6.73 (d, 1H); 7.45 (dd, 1H).

Stage 2: 6-dimethylaminopyridine-2-carbaldehyde 0.60 g of (6-[1,3]dioxolan-2-yl-pyridin-2-yl) dimethylamine (3.09 mmol) is mixed in 10 ml of an aqueous solution of formic acid at 80% and then the solution is heated at 60° C. for 20 hours. The solvents are removed by azeotropic entrainment with toluene, the residue is taken up in water, the mixture is cooled to 0° C. and then the medium is basified by addition of potassium carbonate. The mixture is extracted with ethyl acetate, the organic phase is washed with water and then with a saturated aqueous solution of sodium chloride, dried over magnesium sulfate, filtered, and the solvent is evaporated under vacuum. The title product is obtained in the form of a yellow oil (0.43 g) which is used in the next stage without further purification.

$^1$H NMR (CDCl$_3$) δ: 3.12 (s, 6H); 6.68 (d, 1H); 7.18 (d, 1H); 7.55 (dt, 1H); 9.87 (s, 1H).

IR film σ: 1697 cm$^{-1}$ (C=O).

EXAMPLE 3

Preparation of 6-furan-2-yl-pyridine-2-carbaldehyde (IVd-1)

Stage 1: 2-furan-2-yl-6-methylpyridine 40 ml of a 1.6 M solution of n-butyllithium in hexane are introduced dropwise into a solution of 4.36 ml of furan (60 mmol) and 40 ml of tetrahydrofuran cooled to 0° C. The solution is stirred for 3 hours at 0° C. and then it is cooled to −40° C. before introducing 120 ml of a 0.5 M solution of zinc dichloride in tetrahydrofuran. The mixture is stirred for 2 hours at room temperature and then the reaction mixture is added to a solution of 9.17 g of trifluoromethanesulfonic acid 6-methylpyridin-2-yl ester (40 mmol) in 20 ml of tetrahydrofuran containing 2.30 g of tetrakis-(triphenylphosphine)palladium (2 mmol). The reaction mixture is maintained under reflux for 2 hours under nitrogen and then cooled and extracted with 1N HCl. The acidic aqueous phase is neutralized with 10N NaOH and then extracted with ethyl acetate. The organic phase is washed with water, dried over magnesium sulfate, filtered and the solvent evaporated off. The expected product is isolated by rectification under reduced pressure.

b.p.$_{5.6 \times 10^{-2}}$=100–105° C.

5.20 g of a colorless oil are recovered.

Yield: 81.5%

$^1$H NMR (CDCl$_3$) δ: 2.56 (s, 3H); 6.48 (dd, 1H); 6.99 (m, 2H); 7.50 (m, 3H).

Stage 2: 2-furan-2-yl-6-methylpyridine 1-oxide 4.90 g of metachloroperbenzoic acid are added in portions to a solution of 2.20 g of 2-furan-2-yl-6-methylpyridine (13.8 mmol) in 50 ml of chloroform cooled to 0° C. The mixture is stirred for 12 hours at room temperature and then the precipitate is removed by filtration and the filtrate is washed with a 5% aqueous solution of sodium bicarbonate. After drying over magnesium sulfate, filtration and evaporation, the title product is isolated by chromatography on a silica column (eluent: chloroform/methanol; 99:1). 1.25 g of a white powder are recovered.

Yield: 52% m.p.: 79° C.

$^1$H NMR (CDCl$_3$) δ: 2.58 (s, 3H); 6.60 (q, 1H); 7.18 (m, 2H); 7.58 (d, 1H); 7.85 (dd, 1H); 8.03 (d, 1H).

Stage 3: (6-furan-2-yl-pyridin-2-yl)methanol 2.75 g of 2-furan-2-yl-6-methylpyridine 1-oxide (15.7 mmol) are dissolved in 27 ml of tetrahydrofuran. 6.65 ml of trifluoroacetic anhydride (47.1 mmol) are added to the solution cooled to 0° C. under a nitrogen atmosphere. The mixture is stirred for 12 hours at room temperature and then 25 ml of a 4N aqueous solution of sodium hydroxide are added. The tetrahydrofuran is evaporated off, the residue is taken up in a saturated aqueous solution of sodium chloride and then the mixture is extracted with chloroform. The organic phase is dried over magnesium sulfate, filtered and concentrated under vacuum. The title product is isolated by chromatography on a silica column (eluent: chloroform/ ethyl acetate; 90:10). 2.03 g of a yellow oil are recovered.

Yield: 73.8%

$^1$H NMR (CDCl$_3$) δ: 3.99 (bs, 1H(exchangeable)); 4.74 (s, 2H); 6.53 (q, 1H); 7.09 (m, 2H); 7.57 (m, 2H); 7.71 (t, 1H).

Stage 4: 6-furan-2-yl-pyridine-2-carbaldehyde 8 g of manganese dioxide are added to a solution of 2 g of (6-furan-2-yl-pyridin-2-yl)methanol (11.4 mmol) and 50 ml of chloroform. The reaction mixture is heated under reflux for 1 hour 30 minutes with removal of the water formed continuously. The solid in suspension is removed by filtration on celite and then the solvent is evaporated off. The title product is isolated by chromatography on a silica column (eluent: chloroform). 1.45 g of a yellow solid are recovered.

Yield: 73.4% m.p.: 46–48° C.

$^1$H NMR (CDCl$_3$) δ: 6.55 (q, 1H); 7.16 (d, 1H); 7.55 (d, 1H); 7.82 (m, 3H); 10.07 (s, 1H).

IR (KBr) σ: 1717 cm$^{-1}$ (C=O).

EXAMPLE 4

6-furan-3-yl-pyridine-2-carbaldehyde (IVd-2)

By carrying out the procedure as in Example 3 but replacing in stage 1 the 2-lithiofuran with 3-lithiofuran obtained by halogen/metal exchange from 3-bromofuran, the title compound is prepared.

m.p.: 59–61° C.

$^1$H NMR (CDCl$_3$) δ: 6.94 (q, 1H); 7.54 (t, 1H); 7.68 (dd, 1H); 7.83 (m, 2H); 8.12 (s, 1H); 10.05 (s, 1H).

IR (KBr) σ: 1713 cm$^{-1}$ (C=O).

EXAMPLE 5

6-(1H-pyrrol-2-yl)-pyridine-2-carbaldehyde (IVe-1)

Stage 1: 2-chloro-6-(2-trimethylsilanyl-ethoxymethoxymethyl)pyridine 3.20 ml of chloromethyl-2-(trimethylsilyl)ethyl ether (18.2 mmol) are added dropwise to a solution containing 2.50 g of (6-chloropyridin-2-yl)methanol (17.4 mmol), 3.30 ml of diisopropylethylamine (19.1 mmol) and 20 ml of dichloromethane cooled to 0° C. maintained under a nitrogen atmosphere. The mixture is stirred for 3 hours at room temperature and then the dichloromethane is evaporated off, the residue is taken up in water, the mixture is extracted with diethyl ether, the organic phase is washed with water and then dried over sodium sulfate. After filtration and evaporation of the solvent, the title product is isolated by chromatography on a silica column (eluent: dichloromethane).

3.65 g of a colorless oil are recovered.

Yield: 76.6%

$^1$H NMR (CDCl$_3$) δ: 0 (S, 9H); 0.95 (t, 2H); 3.68 (t, 2H); 4.67 (s, 2H); 4.80 (s, 2H); 7.24 (d, 1H); 7.35 (d, 1H); 7.64 (t, 1H).

Stage 2: 2-benzyloxy-6-(2-trimethylsilanyl-ethoxymethoxymethyl)pyridine 2.10 ml of benzyl alcohol (19.9 mmol) diluted in 3 ml of N,N-dimethylformamide are added dropwise to a suspension of 0.91 g of sodium hydride (22.6 mmol) in 20 ml of N,N-dimethylformamide cooled to 0° C. and maintained under a nitrogen atmosphere. The mixture is stirred for 1 hour 30 minutes at 0° C. and then a solution of 3.65 g of 2-chloro-6-(2-trimethylsilanyl-ethoxymethoxymethyl) pyridine (13.3 mmol) in 3 ml of N,N-dimethylformamide is added dropwise. The reaction is taken to 40° C. for 12 hours, the reaction mixture is poured into ice-cold water, extracted with diethyl ether and then the combined organic phases are washed with water and dried over magnesium sulfate. After filtration and evaporation of the solvent, the title product is isolated by chromatography on a silica column (eluent: dichloromethane/hexane; 60:40). 3 g of a colorless oil are recovered.

Yield: 65.3%

$^1$H NMR (CDCl$_3$) δ: 0 (s, 9H); 0.94 (t, 2H); 3.67 (t, 2H); 4.61 (s, 2H); 4.80 (s, 2H); 5.35 (s, 2H); 6.66 (d, 1H); 6.97 (d, 1H); 7.34 (m, 3H); 7.42 (m, 2H); 7.54 (t, 1H).

Stage 3: 6-(2-trimethylsilanyl-ethoxymethoxymethyl)-pyridin-2-ol 7 g of Raney Nickel are added to a solution of 7 g of 2-benzyloxy-6-(2-trimethylsilanyl-ethoxymethoxy-methyl) pyridine in 75 ml of ethanol saturated with hydrogen. The suspension is stirred vigorously under a low hydrogen pressure at room temperature for 1 hour 30 minutes. The solid in suspension is removed by filtration on celite and then the ethanol is evaporated off. The title product is isolated by chromatography on a silica column (eluent: dichloromethane/methanol; 98:2). 4 g of a colorless oil are recovered.

Yield: 76.8%

$^1$H NMR (CDCl$_3$) δ: 0 (s, 9H); 0.93 (t, 2H); 3.61 (t, 2H); 4.50 (s, 1H); 4.75 (s, 2H); 6.21 (d, 1H); 6.47 (d, 1H); 7.36 (d, 1H); 7.41 (d, 1H); 12.28 (s, 1H (exchangeable)).

Stage 4: Trifluoromethanesulfonic Acid 6-(2-trimethyl-silanyl-ethoxymethoxymethyl)pyridin-2-yl Ester 2.63 ml of trifluoromethansulfonic anhydride (14.9 mmol) are added dropwise to a solution of 3.80 g of 6-(2-trimethylsilanyl-ethoxymethoxymethyl)pyridin-2-ol (14.8 mmol) and 35 ml of pyridine containing 0.10 g of 4-N,N-dimethylaminopyridine maintained at 0° C. under a nitrogen atmosphere. The solution is stirred for 2 hours at 0° C. and then the mixture is poured into ice-cold water and extracted with diethyl ether. The organic phase is washed with an aqueous solution of potassium hydrogen sulfate and then with water, dried over magnesium sulfate, filtered and evaporated off. The title product is isolated by chromatography on a silica column (eluent: dichloromethane). 4.30 g of a colorless oil are recovered.

Yield: 75%

$^1$H NMR (CDCl$_3$) δ: 0 (s, 9H); 0.93 (t, 2H); 3.66 (t, 2H); 4.68 (s, 2H); 4.80 (s, 2H); 7.05 (d, 1H); 7.52 (d, 1H); 7.87 (t, 1H).

Stage 5: 2-[6-(2-trimethylsilanyl-ethoxymethoxymethyl) pyridin-2-yl]pyrrole-1-carboxylic Acid tert-butyl Ester The preparation of 1-tert-butoxycarbonylpyrrol-2-yl boronic acid is carried out according to the method described in Synthesis, 1991, 613–15.

9.68 g of thallium carbonate (20.6 mmol), 1 g of tetrakis (triphenylposphine)palladium (0.86 mmol) and 2.45 g of 1-tert-butoxycarbonylpyrrol-2-yl boronic acid (11.6 mmol) are added to a solution of 4 g of trifluoromethanesulfonic acid 6-(2-trimethylsilanyl-ethoxymethoxymethyl)pyridin-2-yl ester (10.3 mmol) and 40 ml of benzene degassed by bubbling of nitrogen. The mixture is stirred for 23 hours under an argon atmosphere. The insoluble matter is removed by filtration on celite and then the solution concentrated under vacuum. The title product is isolated by chromatography on a silica column (eluent: dichloromethane/ethyl acetate; 99:1). 3.90 g of a yellow oil are recovered.

Yield: 93.6%

$^1$H NMR (CDCl$_3$) δ: 0 (s, 9H); 0.94 (t, 2H); 1.32 (s, 9H); 3.67 (t, 2H); 4.73 (s, 2H); 4.82 (s, 2H); 6.21 (t, 1H); 6.37 (m, 1H); 7.27 (d, 1H); 7.32 (m, 1H); 7.34 (d, 1H); 7.68 (t, 1H).

Stage 6: [6-(1H-pyrrol-2-yl)pyridin-2-yl]methanol 3 g of 2-[6-(2-trimethylsilanyl-ethoxymethoxy-methyl)pyridin-2-yl]pyrrole-1-carboxylic acid tert-butyl ester (7.41 mmol) are added to a solution of 3 ml of 1.1 M tetrabutylammonium fluoride in tetrahydrofuran, 45 ml of tetrahydrofuran and 5 ml of hexamethylphosphoramide, containing 10 g of molecular sieve (4 angstrom). The mixture is stirred at 45° C. under argon for 8 hours. After filtration of the insoluble matter on celite, the tetrahydrofuran is evaporated off. The title product is purified by chromatography on a silica column (eluent: dichloromethane/ethyl acetate; 99:1). 0.50 g of a white solid is recovered.

Yield: 38.7% m.p.: 73–75° C.

$^1$H NMR (CDCl$_3$) δ: 3.61 (bs, 1H); 4.74 (s, 2H); 6.30 (dd, 1H); 6.73 (m, 1H); 6.92 (m, 1H); 6.98 (d, 1H); 7.45 (d, 1H); 7.62 (t, 1H); 9.56 (bs, 1H).

Stage 7: 6-(1H-pyrrol-2-yl)pyridine-2-carbaldehyde 0.75 g of manganese dioxide (8.61 mmol) is added to a solution of 0.30 g of [6-(1H-pyrrol-2-yl)pyridin-2-yl]methanol (1.72 mmol) in 6 ml of dichloromethane. The suspension is stirred vigorously for 3 hours at room temperature and then the insoluble matter is removed by filtration on celite. After evaporation of the dichloromethane, the residue is purified by chromatography on a silica column (eluent: dichloromethane). 0.20 g of a white powder is recovered.

Yield: 69% m.p.: 112–113° C.

$^1$H NMR (CDCl$_3$) δ: 6.31 (dd, 1H); 6.77 (m, 1H); 6.95 (m, 1H); 7.63–7.81 (m, 3H); 9.67 (bs, 1H); 10.03 (s, 1H).

IR (KBr) σ: 1701 cm$^{-1}$ (C=O).

EXAMPLE 6

Preparation of 6-thiophen-2-yl-pyridine-2-carbaldehyde (IVe-2)

By carrying out the procedure as in Example 5 but replacing in stage 5 the 1-tert-butoxycarbonylpyrrol-2-yl boronic acid with thiophen-2-yl boronic acid which is commercially available, the title compound is obtained in the form of a yellow solid.

m.p.: 48–50° C.

$^1$H NMR (CDCl$_3$) δ: 7.15 (d, 1H); 7.46 (dd, 1H); 7.69 (dd, 1H); 7.78–7.88 (m, 3H); 10.16 (s, 1H).

IR (KBr) σ: 1714 cm$^{-1}$ (C=O).

EXAMPLE 7

Preparation of 6-thiazol-2-yl-pyridine-2-carbaldehyde (IVf-1)

Stage 1: 6-[1,3]dioxolan-2-yl-pyridine-2-carbonitrile 3.34 g of 2-[2,3]dioxolan-2-yl-pyridine 1-oxide (19.98 mmol) are dissolved in 40 ml of dichloromethane and then 2.93 ml of cyanotrimethylsilane (21.97 mmol) and 2.53 ml of diethylcarbamoyl chloride (19.96 mmol) are added successively. The solution is stirred for 240 hours at room temperature under a nitrogen atmosphere. The reaction mixture is poured slowly into an ice-cold 10% aqueous solution of potassium carbonate, the mixture is extracted with chloroform and then the organic phase is washed with a 10% aqueous solution of potassium carbonate. The mixture is dried over magnesium sulfate, filtered and the chloroform is evaporated under reduced pressure. The title compound is isolated by chromatography on a silica column (eluent: chloroform). 2.75 g of a white solid are recovered.

Yield: 78.1% m.p.: 64° C.

$^1$H NMR (CDCl$_3$) δ: 4.14 (m, 4H); 5.86 (s, 1H); 7.71 (dd, 1H); 7.78 (dd, 1H); 7.91 (t, 1H).

Stage 2: 6-[1,3]dioxolan-2-yl-pyridine-2-carboximidic Acid Methyl Ester 0.20 g of sodium methoxide (3.7 mmol) is added to a solution of 2 g of 2-[1,3]dioxolan-2-yl-pyridine-2-carbonitrile (11.35 mmol) in 10 ml of methanol. The reaction mixture is stirred for 24 hours under a nitrogen atmosphere. The methanol is evaporated off and then the residue is taken up in a saturated aqueous solution of sodium chloride and the mixture is extracted with ethyl acetate. The organic phase is dried over sodium sulfate, filtered and the solvent evaporated off. 2.30 g of a white solid are obtained, which solid is used directly in the next stage without further purification.

Stage 3: 2-(4,5-dihydrothiazol-2-yl)-6-[1,3]dioxolan-2-yl-pyridine 1 g of 6-[1,3]dioxolan-2-yl-pyridine-2-carboximidic acid methyl ester (4.80 mmol) and 0.47 g of 2-aminoethanethiol (2.16 mmol) are mixed. The mixture is heated at 130° C. for 1 hour 30 minutes. The reaction mixture is taken up in chloroform, washed with water and then dried over magnesium sulfate. After filtration and evaporation of the solvent, the title product is isolated by chromatography on a silica column (eluent: chloroform/methanol; 98:2). 1.10 g of solid are recovered.

Yield: 97% m.p.: 50–52° C.

$^1$H NMR (CDCl$_3$) δ: 3.36 (t, 2H); 4.15 (m, 4H); 4.55 (t, 2H); 5.91 (s, 1H); 7.60 (dd, 1H); 7.81 (t, 1H); 8.03 (dd, 1H).

Stage 4: 2-thiazol-2-yl-6-[1,3]dioxolan-2-yl-pyridine 10 g of nickel peroxide hydrate are added in 1 g portions over 20 hours to a solution of 1.33 g of 2-(4,5-dihydrothiazol-2-yl)-6-[1,3]dioxolan-2-yl-pyridine (5.62 mmol) in 50 ml of benzene maintained under reflux with removal of the water formed continuously. The insoluble matter is removed by filtration on celite and then the solvent is evaporated off. The title product is isolated by chromatography on a silica column (eluent: chloroform/ethyl acetate; 85:15). 0.42 g of a white solid is recovered.

Yield: 31.5% m.p.: 71° C.

$^1$H NMR (CDCl$_3$) δ: 4.16 (m, 4H); 5.91 (s, 1H); 7.42 (d, 1H); 7.54 (dd, 1H); 7.81 (d, 1H); 7.89 (t, 1H); 8.17 (dd, 1H).

Stage 5: 6-thiazol-2-yl-pyridine-2-carbaldehyde

A solution of 0.93 g of 2-thiazol-2-yl-6-[1,3]dioxolan-2-yl-pyridine (3.97 mmol) in 8 ml of formic acid and 2 ml of water is heated at 60° C. for 1 hour 30 minutes. The solvents are removed by azeotropic entrainment with toluene. The residue is taken up in ice-cold water, the mixture is neutralized with a 4N aqueous solution of sodium hydroxide and then the mixture is extracted with ethyl acetate. The organic phase is washed with a saturated solution of sodium chloride and then dried over magnesium sulfate, filtered and the solvent evaporated off. The title product is crystallized by addition of isopropyl ether. 0.59 g of a white solid is recovered.

Yield: 78% m.p.: 91° C.

$^1$H NMR (CDCl$_3$) δ: 7.48 (d, 1H); 7.96 (m, 3H); 8.38 (m, 1H); 10.09 (s, 1H).

IR (KBr) σ: 1705 cm$^{-1}$ (C=O)

EXAMPLE 8

Preparation of 2-[1,3]dioxolan-2-yl-6-(1H-imidazol-2-yl)pyridine-2-carbaldehyde (IVf-2)

By carrying out the procedure as in Example 7 but replacing in stage 3 the 2-aminoethanethiol with ethylenediamine and in stage 4 the nickel peroxide hydrate with barium permanganate, the title compound is obtained in the form of a yellow solid.

m.p.: 148° C.

$^1$H NMR (CDCl$_3$) δ: 4.77 (s, 1H (exchangeable)); 7.22 (d, 2H); 7.89 (m, 2H); 8.35 (d, 1H); 10.03 (s, 1H). IR (KBr) σ: 1704 cm$^{-1}$ (C=O).

EXAMPLE 9

Preparation of 6-(methyl-5-oxadiazol-3-yl)pyridine-2-carbaldehyde (IVg-1)

Stage 1: 6-[1,3]dioxolan-2-yl-N-hydroxypyridine-2-carboxamidine 0.88 g of 2-[1,3]dioxolan-2-yl-pyridine-2-carbonitrile (4.99 mmol), 1.74 g of hydroxylamine hydrochloride (25 mmol) and 3.45 g of potassium carbonate (25 mmol) are mixed in 15 ml of ethanol and then the reaction mixture is heated under reflux for 4 hours. After evaporation of the ethanol, the title product is crystallized by addition of water to the residue. 0.80 g of a colorless powder is recovered.

Yield: 76.6% m.p.: 148° C.

$^1$H NMR (DMSOd6) δ: 4.06 (m, 4H); 5.77 (s, 1H); 5.82 (s, 2H (exchangeable)); 7.52 (m, 1H); 7.85 (m, 2H); 9.98 (s, 1H (exchangeable)).

Stage 2: 2-[1,3]dioxolan-2-yl-6-(methyl-5-oxadiazol-3-yl)pyridine 0.30 g of 6-[1,3]dioxolan-2-yl-N-hydroxy-pyridine-2-carboxamidine (1.43 mmol) is dissolved in 0.60 ml of pyridine and then 0.15 ml of acetyl chloride (2.11 mmol) is added. The reaction mixture is heated at a reflux temperature of the solvent for 2 hours 15 minutes. The mixture is poured into an ice-cold aqueous solution of potassium hydrogen sulfate and then extracted with ethyl acetate. The organic phase is washed with a saturated aqueous solution of sodium chloride, dried over magnesium sulfate, filtered and the ethyl acetate is evaporated off. The title product is isolated by chromatography on a silica column (eluent: chloroform/ethyl acetate; 80:20).

0.15 g of a white powder is recovered.

Yield: 45% m.p.: 90–91° C.

$^1$H NMR (CDCl$_3$) δ: 2.67 (s, 3H); 4.13 (m, 4H); 5.95 (s, 1H); 7.68 (dd, 1H); 7.87 (t, 1H); 8.07 (t, 1H).

Stage 3: 6-(methyl-5-oxadiazol-3-yl)pyridine-2-carbaldehyde

The acid hydrolysis of 0.74 g of 6-[1,3]dioxolan-2-yl-N-hydroxypyridine-2-carboxamidine (3.17 mmol) is carried out according to a protocol similar to that used in stage 5 of Example 7.

0.42g of the title compound is obtained in the form of a white powder.

Yield: 70% m.p.: 123° C.

$^1$H NMR (CDCl$_3$) δ: 2.74 (s, 3H); 8.04 (t, 1H); 8.10 (dd, 1H); 8.34 (dd, 1H); 10.23 (s, 1H).

IR (KBr) σ: 1703 cm$^{-1}$ (C=O).

EXAMPLE 10

Preparation of 6-(1H-pyrazol-3-yl)-pyridine-2-carbaldehyde (IVh-1a)

Stage 1: 1-(6-[1,3]dioxolan-2-yl-pyridine-2-yl)-ethanone 0.88 g of 2-[1,3]dioxolan-2-yl-pyridine-2-carbonitrile (4.99 mmol) is dissolved in 10 ml of tetrahydrofuran. 3.50 ml of a 3M solution of methylmagnesium bromide in diethyl ether are introduced dropwise into the solution cooled to −10° C. The reaction mixture is stirred for 3 hours at room temperature under a nitrogen atmosphere. The mixture is poured into a saturated aqueous solution of ammonium chloride, the mixture is extracted with ethyl acetate, the organic phase is washed with a saturated aqueous solution of ammonium chloride and then dried over magnesium sulfate, filtered and concentrated under vacuum. The title product is isolated by chromatography on a silica column (eluent: chloroform). 0.80 g of a yellow oil is recovered.

Yield: 83%

$^1$H NMR (CDCl$_3$) δ: Error? Undefined marker. 2.72 (s, 3H); 4.15 (m, 4H); 5.89 (s, 1H); 7.70 (dd, 1H); 7.86 (t, 1H); 8.01 (dd, 1H).

IR (film) σ: 1700 cm$^{-1}$ (C=O)

Stage 2: 3-dimethylamino-1-(6-[1,3]dioxolan-2-yl-pyridin-2-yl)propenone 0.80 g of 1-(6-[1,3]dioxolan-2-yl-pyridin-2-yl)ethanone (4.14 mmol) and 1 ml of N,N-dimethylformamide dimethyl acetal (7.53 mmol) are mixed. The mixture is heated under reflux for 12 hours and the excess N,N-dimethylformamide dimethyl acetal is evaporated under vacuum.

The title product is obtained in the form of an orange-colored oil which is used directly in the next stage without further purification.

Stage 3: 2-[1,3]dioxolan-2-yl-6-(1H-pyrazol-3-yl)pyridine

The crude product obtained in stage 2 is taken up in 5 ml of ethanol and then 0.80 ml of hydrazine hydrate (25.68 mmol) is added. The solution is heated under reflux for 5 minutes. The ethanol is evaporated off, the residue is taken up in water and the mixture is extracted with chloroform. The organic phase is washed with water, dried over magnesium sulfate, filtered and evaporated off. The title product is isolated by chromatography on a silica column (eluent: chloroform/methanol; 98:2). 0.65 g of a pale yellow gum is obtained.

Yield for stage 2 and stage 3 combined: 72.3%

$^1$H NMR (CDCl$_3$) δ: 4.15 (m, 4H); 5.90 (s, 1H); 6.80 (d, 1H); 7.48 (dd, 1H); 7.65 (d, 1H); 7.76 (m, 2H); 11.23 (bs, 1H).

Stage 4: 6-(1H-pyrazol-3-yl)pyridine-2-carbaldehyde

The deprotection of the acetal function of 2-[1,3]dioxolan-2-yl-6-(1H-pyrazol-3-yl)pyridine is carried out on 0.65 g of product (2.99 mmol) according to a protocol similar to that used in stage 5 of Example 7. The title compound is isolated by chromatography on a silica column (eluent: chloroform/methanol; 98:2). 0.31 g of a white foam is obtained.

Yield: 59.9%

$^1$H NMR (DMSOd6) δ: 6.91 (d, 1H); 7.80 (m, 2H); 8.03 (t, 1H); 8.20 (d, 1H); 9.99 (s, 1H); 13.17 (bs, 1H (exchangeable)).

IR (film) σ: 1710 cm$^{-1}$ (C=O).

EXAMPLE 11

Preparation of 6-(1-methylpyrazol-3-yl)pyridine-2-carbaldehyde (IVh-2a)

Stage 1: 2-[1,3]dioxolan-2-yl-6-(1-methylpyrazol-3-yl)pyridine 2.50 g of 2-[1,3]dioxolan-2-yl-6-(1H-pyrazol-3-yl)pyridine (11.5 mmol) dissolved in 4 ml of N,N-dimethylformamide are added dropwise to a suspension of 0.48 g of sodium hydride (20 mmol) in 4 ml of N,N-dimethylformamide. The reaction mixture is stirred for 1 hour under a nitrogen atmosphere and then 0.93 ml of methyl iodide (15 mmol) diluted in 1 ml of N,N-dimethylformamide is added dropwise to the reaction mixture. The solution is stirred for 12 hours at room temperature and then the mixture is poured in ice-cold water and the mixture is extracted with ethyl acetate. The organic phase is washed with a saturated aqueous solution of sodium chloride, dried over magnesium sulfate, filtered and concentrated under vacuum. The title product is isolated by chromatography on a silica column (eluent: chloroform/methanol; 99:1). 0.83 g of a white solid is obtained.

Yield: 31% m.p.: 88° C.

$^1$H NMR (CDCl$_3$) δ: 3.99 (s, 3H); 4.11 (m, 4H); 5.90 (s, 1H); 6.91 (d, 1H); 7.36 (d, 1H); 7.42 (dd, 1H); 7.72 (t, 1H); 7.90 (dd, 1H).

Stage 2: 6-(1-methylpyrazol-3-yl)pyridine-2-carbaldehyde

The deprotection of 0.77 g of 2-[1,3]dioxolan-2-yl-6-(1-methylpyrazol-3-yl)pyridine (3.31 mmol) according to a protocol similar to that used in stage 5 of Example 7 gives 0.48 g of the title product (2.51 mmol) after purification by chromatography on a silica column (eluent: ethyl acetate).

Yield: 75.8% m.p.: 98–100° C.

$^1$H NMR (CDCl$_3$) δ: 3.98 (s, 3H); 6.93 (d, 1H); 7.42 (d, 1H); 7.84 (m, 2H); 8.09 (dd, 1H); 10.12 (s, 1H);

IR (KBr) σ: 1710 cm$^{-1}$ (C=O).

EXAMPLE 12

Preparation of 6-isopropylpyridine-2-carbaldehyde (IVi)

Stage 1: 2-[1,3]dioxolan-2-yl-6-isopropenylpyridine 1.62 g of potassium tert-butoxide (14.4 mmol) are added in portions to a suspension of 5.25 g of (methyl) triphenylphosphonium bromide (14.7 mmol) in 30 ml of tetrahydrofuran maintained under a nitrogen atmosphere. The mixture is stirred for 45 minutes and then a solution of 0.95 g of 1-(6-[1,3]dioxolan-2-yl-pyridin-2-yl)ethanone (4.92 mmol) in 5 ml of tetra-hydrofuran is introduced dropwise. The mixture is stirred for 12 hours at room temperature and then it is poured into a saturated aqueous solution of ammonium chloride. The mixture is extracted with ethyl acetate, the organic phase is washed with a saturated aqueous solution of sodium chloride, dried over magnesium sulfate, filtered and concentrated under vacuum. The residue is taken up in diethyl ether and the precipitate formed is removed by filtration. After evaporation of the solvent, the title product is isolated by chromatography on a silica column (eluent: hexane/ethyl acetate; 85:15). 0.67 g of a pale yellow oil is obtained.

Yield: 71.6%

$^1$H NMR (CDCl$_3$) δ: 2.22 (s, 3H); 4.16 (m, 4H); 5.31 (m, 1H); 5.87 (s, 1H); 5.91 (m, 1H); 7.44 (m, 2H); 7.70 (t, 1H).

Stage 2: 2-[1,3]dioxolan-2-yl-6-isopropylpyridine

A suspension of 0.60 g of 2-[1,3]dioxolan-2-yl-6-isopropenylpyridine (3.15 mmol) and 0.10 g of 10% palladium on carbon, in 7 ml of methanol is stirred vigorously under a low hydrogen pressure for 4 hours at room temperature. The solid is removed by filtration on celite and then the methanol is evaporated off. The title product is isolated by chromatography on a silica column (eluent: chloroform/ethyl acetate; 97:3). 0.40 g of a pale yellow oil is obtained.

Yield: 66%

$^1$H NMR (CDCl$_3$) δ: 1.30 (d, 6H); 3.07 (m, 1H); 4.13 (m, 4H); 5.83 (s, 1H); 7.17 (d, 1H); 7.36 (d, 1H); 7.66 (t, 1H).

Stage 3: 6-isopropylpyridine-2-carbaldehyde

The deprotection of 0.36 g of 2-[1,3]dioxolan-2-yl-6-isopropylpyridine (1.87 mmol) according to a protocol similar to that used in stage 5 of Example 7 gives 0.31 g of the title product (1.81 mmol) after purification by chromatography on a silica column (eluent: chloroform).

Yield: 96.8%

$^1$H NMR (CDCl$_3$) δ: 1.34 (d, 6H); 3.10 (m, 1H); 7.37 (m, 1H); 7.73 (d, 2H); 10.03 (s, 1H).

IR (film) σ: 1712 cm$^{-1}$ (C=O).

EXAMPLE 13

Preparation of 6-oxazol-5-yl-pyridine-2-carbaldehyde (IVk)

Stage 1: 2-[1,3]dioxolan-2-yl-6-oxazol-5-yl-pyridine 1 g of 6-[1,3]dioxolan-2-yl-pyridine-2-carbaldehyde (5.58 mmol), 1.10 g of tosylmethyl isocyanate (5.63 mmol) and 0.80 g of potassium carbonate (5.79 mmol) are mixed in 15 ml of methanol. The suspension is heated under reflux for 2 hours. The methanol is separated off, the residue is taken up in a saturated aqueous solution of sodium chloride and the mixture is extracted with ethyl acetate. The organic phase is dried over magnesium sulfate, filtered and then concentrated under vacuum. The title product is isolated by chromatography on a silica column (eluent: hexane/ethyl acetate; 50:50). 1.14 g of a yellow oil are obtained.

Yield: 93.6%

$^1$H NMR (CDCl$_3$) δ: 4.13 (m, 4H); 5.86 (s, 1H); 7.48 (d, 1H); 7.63 (d, 1H); 7.77 (m, 2H); 7.95 (s, 1H).

Stage 2: 6-oxazol-5-yl-pyridine-2-carbaldehyde

The deprotection of 0.95 g of 2-[1,3]dioxolan-2-yl-6-oxazol-5-yl-pyridine (4.35 mmol) according to a protocol similar to that used in stage 5 of Example 7 gives 0.32 g of the title product after purification by chromatography on a silica column (eluent: chloroform/ethyl acetate; 80:20).

Yield: 42.3% m.p.: 151° C.

$^1$H NMR (CDCl$_3$) δ: 7.81–8.01 (m, 5H); 10.08 (s, 1H).

IR (KBr) σ: 1703 cm$^{-1}$ (C=O).

EXAMPLE 14

Preparation of 6-cyclopropylpyridine-2-carbaldehyde (IVl)

Stage 1: 2-[1,3]dioxolan-2-yl-vinylpyridine

A mixture of 3.10 g of 6-[1,3]dioxolan-2-yl-pyridine-2-carbaldehyde (17.3 mmol), 9.26 g of (methyl) triphenylphosphonium bromide (25.9 mmol) and 4.80 g of potassium carbonate (34.8 mmol) in 60 ml of 1,4-dioxane is maintained under reflux for 5 hours. The solid is removed by filtration and then the solvent is evaporated off. The residue is taken up in ethyl acetate, the solution is washed with water and then with a saturated aqueous solution of sodium chloride, dried over magnesium sulfate and filtered. After evaporation of the solvent, the title compound is isolated by chromatography on a silica column (eluent: hexane/ethyl acetate; 80:20). 1.63 g of a yellow oil are obtained.

Yield: 53.2%

$^1$H NMR (CDCl$_3$) δ: 5.47 (dd, 1H); 5.83 (s, 1H); 6.18 (dd, 1H); 6.83 (dd, 1H); 7.36 (m, 2H); 7.67 (t, 1H).

Stage 2: 2-cyclopropyl-6-[1,3]dioxolan-2-yl-pyridine 5.60 ml of a 1.6 M solution of n-butyllithium in hexane are introduced dropwise into a suspension of 2.71 g of trimethylsulfonium iodide (13.3 mmol) in 25 ml of tetrahydrofuran cooled to −15° C. The solution is stirred at −15° C. for 20 minutes under nitrogen, and then a solution of 1.57 g of 2-[1,3]dioxolan-2-yl-6-vinylpyridine (8.90 mmol) in 5 ml of tetrahydrofuran is added dropwise. After stirring for 1 hour at −15° C., the suspension is stirred for 3 hours at room temperature. The tetrahydrofuran is evaporated off, the residue is taken up in water and the mixture is extracted with ethyl acetate. The organic phase is washed with a saturated aqueous solution of sodium chloride, dried over magnesium sulfate, filtered and concentrated under vacuum. The title product is isolated by chromatography on a silica column (eluent: hexane/ethyl acetate; 50:50). 1.24 g of a colorless oil are obtained.

Yield: 73%

$^1$H NMR (CDCl$_3$) δ: 0.98 (m, 4H); 2.06 (m, 1H); 4.09 (m, 4H); 5.76 (s, 1H); 7.03 (dd, 1H); 7.25 (dd, 1H); 7.55 (t, 1H).

Stage 3: 6-cyclopropylpyridine-2-carbaldehyde

The deprotection of 1.14 g of 2-cyclopropyl-6-[1,3] dioxolan-2-yl-pyridine (5.96 mmol) according to a protocol similar to that used in stage 5 of Example 7 gives 0.75 g of the title product after purification by chromatography on a silica column (eluent: hexane/ethyl acetate; 90:10).

Yield: 85%

$^1$H NMR (CDCl$_3$) δ: 1.09 (m, 4H); 2.10 (m, 1H); 7.33 (m, 1H); 7.68 (m, 2H); 9.96 (s, 1H).

IR (film) σ: 1713 cm$^{-1}$ (C=O).

EXAMPLE 15

Preparation of 6-(1-fluoroethyl)-pyridine-2-carbaldehyde (IVj)

Stage 1: 1-(6-[1,3]dioxolan-2-yl-pyridin-2-yl)ethanol 0.50 g of potassium borohydride (9.27 mmol) is added in portions to a solution of 0.90 g of 1-(6-[1,3]dioxolan-2-yl-pyridin-2-yl)ethanone (4.66 mmol) in 15 ml of methanol. The mixture is stirred for 12 hours at room temperature and then methanol is evaporated off and the residue is taken up in chloroform. The organic phase is washed with water and then dried over sodium sulfate, filtered, and concentrated under vacuum. 0.70 g of a pale yellow oil is obtained, which oil is used in the next stage without further purification. $^1$H NMR (CDCl$_3$) δ: 1.47 (d, 3H); 1.84 (s, 1H(exchangeable)); 4.11 (m, 4H); 4.88 (m, 1H); 5.82 (s, 1H); 7.25 (d, 1H); 7.41 (d, 1H); 7.75 (t, 1H).

Stage 2: 2-[1,3]dioxolan-2-yl-6-(1-fluoroethyl)pyridine 0.81 ml of diethylamine trifluorosulfide (6.14 mmol) is added to a solution of 0.60 g of 1-(6-[1,3]-dioxolan-2-yl-pyridin-2-yl)ethanol (3.07 mmol) in 25 ml of dichloromethane cooled to −78° C. and maintained under a nitrogen atmosphere. The mixture is stirred for 30 minutes at −78° C. and then for 2 hours at room temperature. The mixture is poured slowly into a 10% aqueous solution of sodium bicarbonate. The organic phase is dried over magnesium sulfate, filtered and the solvent is evaporated off. The title product is isolated by chromatography on a silica column (eluent: chloroform). 0.42 g of a yellow oil is obtained. Yield for the 2 stages combined: 53.4%

$^1$H NMR (CDCl$_3$) δ: 1.69 (dd, 3H); 4.11 (m, 4H); 5.77 (dq, 1H); 5.83 (s, 1H); 7.48 (d, 2H); 7.79 (t, 1H).

Stage 3: 6-(1-fluoroethyl)pyridine-2-carbaldehyde

The deprotection of 0.40 g of 2-[1,3]dioxolan-2-yl-6-(1-fluoroethyl)pyridine (2 mmol) according to a protocol similar to that used in stage 5 of Example 7 gives 0.32 g of the title product in the form of a yellow oil used in the next stage without further purification.

$^1$H NMR (CDCl$_3$) δ: 1.72 (dd, 3H); 5.75 (dq, 1H); 7.70 (dd, 1H); 7.90 (m, 2H); 10.03 (s, 1H).

IR (film) σ: 1715 cm$^{-1}$ (C=O).

EXAMPLE 16

Preparation of 6-(1-fluoromethyl)-pyridine-2-carbaldehyde (IVm-1)

By carrying out the procedure as in Example 15 but replacing the 1-(6-[1,3]dioxolan-2-yl-pyridin-2-yl)ethanol with 1-(6-[1,3]dioxolan-2-yl-pyridin-2-yl)methanol in stage 2, the title compound is obtained in the form of a yellow solid.

m.p.: 60° C.

$^1$H NMR (CDCl$_3$) δ: 5.55 (d, 2H, J=47 Hz); 7.68 (dd, 1H); 7.90 (m, 2H); 15.35 (s, 1H).

IR (KBr) σ: 1721 cm$^{-1}$ (C=O).

EXAMPLE 17

Preparation of 6-(1,1-difluoromethyl)-pyridine-2-carbaldehyde (IVm-2)

Stage 1: 2-[1,3]dioxolan-2-yl-6-(1,1-difluoro-methyl)pyridine 2.21 ml of diethylamine trifluorosulfide are added dropwise to a solution of 2.40 g of 6-[1,3]-dioxolan-2-yl-pyridine-2-carbaldehyde (13.4 mmol) in 20 ml of chloroform. The mixture is stirred at room temperature under nitrogen for 12 hours and then the mixture is poured into an ice-cold 20% solution of sodium bicarbonate. The organic phase is dried over magnesium sulfate, filtered and concentrated under vacuum. The title product is isolated by chromatography on a silica column (eluent: chloroform). 1.60 g of a yellow oil are obtained.

Yield: 59.3%

$^1$H NMR (CDCl$_3$) δ: 4.11 (m, 4H); 5.85 (s, 1H); 6.65 (t, 1H); 7.63 (m, 2H); 7.88 (t, 1H).

Stage 2: 6-(1,1-difluoromethyl)pyridine-2-carbaldehyde

The deprotection of 0.85 g of 2-[1,3]dioxolan-2-yl-6-(1,1-difluoromethyl)pyridine (4.20 mmol) according to a protocol similar to that used in stage 5 of Example 7 gives 0.70 g of the product in the form of a yellow oil which is used in the next stage without further purification.

$^1$H NMR (CDCl$_3$) δ: 6.69 (t, 1H); 7.85 (m, 1H); 8 03 (m, 2H); 10.05 (s, 1H).

IR (film) σ: 1721 cm$^{-1}$ (C=O)

EXAMPLE 18

Preparation of 6-formylpyridine-2-carboxylic Acid Methyl Ester (IVo)

A solution of 3 g of 6-hydroxymethylpyridine-2-carboxylic acid methyl ester (16.5 mmol) in 70 ml of 1,2-dichloroethane containing 15 g of manganese dioxide (165 mmol) is heated under reflux for 4 hours with removal of the water formed continuously. The solid is removed by filtration on celite and then the dichloromethane is evaporated off. The title product is isolated by chromatography on a silica column (eluent: dichloromethane/ethyl acetate; 70:30). 2.33 g of a yellow oil are recovered.

Yield: 79%

$^1$H NMR (CDCl$_3$) δ: 1.36 (t, 3H); 4.41 (m, 2H); 8.13 (dd, 1H); 8.24 (t, 1H); 8.32 (dd, 1H); 10.02 (s, 1H).

IR (film) σ: 1700 cm$^{-1}$ (C=O).

EXAMPLE 18a

Preparation of 5-methyl-6-methylamino-pyridine-2-carbaldehyde (IVs-1)

Stage 1: (6-chloro-5-methylpyridin-2-yl)methanol 0.40 g of sodium borohydride (10.5 mmol) is added in portions to a solution of 1.20 g of 6-chloro-5-methylpyridine-2-carboxylic acid ethyl ester (6.00 mmol) and 10 ml of ethanol maintained at room temperature. The mixture is stirred for 4 hours and then the mixture is poured into an aqueous solution of sodium chloride and the mixture is extracted with ethyl acetate. The organic phase is dried over sodium sulfate, filtered and concentrated under vacuum. The title product is isolated by chromatography on a silica column (eluent: chloroform). 0.69 g of a colorless oil is recovered.

Yield: 73%

$^1$H NMR (CDCl$_3$) δ: 2.37 (s, 3H); 4.70 (s, 2H); 2.94 (s; broad); 7.17 (d, 1H); 7.55 (d, 1H)

Stage 2: (5-methyl-6-methylaminopyridin-2-yl)methanol 0.96 g of (6-chloro-5-methylpyridin-2-yl)-methanol (6.09 mmol) and 7 ml of methylamine at 33% in ethanol are heated at 120° C in a bomb for 96 hours. 2 ml of methylamine at 33% in ethanol are added every 24 hours. The reaction mixture is concentrated under vacuum and the title compound isolated by chromatography on a silica column (eluent: cyclohexane/ethyl acetate; 40:60).

0.34 g of a white solid is recovered.

Yield: 37% m.p.: 87° C.

$^1$H NMR (CDCl$_3$) δ: 2.06 (s, 3H); 3.05 (d; 3H); 4.13 (s, 1H); 4.24 (s, 1H); 4.59 (d, 2H); 6.39 (d, 1H); 7.18 (d, 1H)

Stage 3: 5-methyl-6-methylaminopyridine-2-carbaldehyde

A suspension of 0.33 g of (5-methyl-6-methylaminopyridin-2-yl)methanol (2.17 mmol) and 1.6 g of manganese dioxide (18.4 mmol) in 12 ml of chloroform is heated under reflux for 1 hour. The insoluble matter is removed by filtration on celite and then the solvent evaporated under vacuum. The title product is purified by chromatography on a silica column (eluent: chloroform). 0.25 g of a yellow solid is recovered.

Yield: 77% m.p.: 79° C.

$^1$H NMR (CDCl$_3$) δ: 2.15 (s, 3H); 3.12 (d, 3H); 4.36 (s, 1H); 7.22 (d, 1H); 7.35 (d, 1H); 9.93 (s, 1H)

EXAMPLE 18b

Preparation of 5-methyl-6-dimethylaminopyridine-2-carbaldehyde (IVs-2)

By carrying out the procedure as in Example 18a but replacing in stage 2 the methylamine at 33% in ethanol with dimethylamine at 33% in ethanol, the title compound obtained is prepared in the form of a yellow oil.

$^1$H NMR (CDCl$_3$) δ: 2.37 (s, 3H); 2.93 (s, 6H); 7.45 (d, 1H); 7.50 (d, 1H); 9.93 (s, 1H)

EXAMPLE 18c

Preparation of 3-methyl-6-dimethylaminopyridine-2-carbaldehyde (IVs-3)

2.65 ml of a 1.6 M solution of n-butyllithium in hexane are introduced into a solution of 0.53 ml of N,N,N'-trimethylethylenediamine (4.24 mmol) and 10 ml of tetrahydrofuran cooled to −60° C. The solution is stirred for 15 minutes at −40° C. and then it is cooled to −70° C. and a solution of 0.50 g of 6-chloropyridine-2-carbaldehyde (3.53 mmol) and 4 ml of tetrahydrofuran is introduced dropwise. The orange-colored solution is stirred for 30 minutes at −70° C. and then 1.28 ml of tetramethylethylenediamine (8.48 mmol) are introduced and then after 10 minutes 5.30 ml of a 1.6M solution of n-butyllithium in hexane are introduced. The brown solution is stirred for 2 hours at −78° C. and 1.50 ml of methyl iodide (25 mmol) are added dropwise. After stirring for one hour at −78° C. and then for 10 minutes at 20° C., the reaction mixture is poured into a saturated aqueous solution of sodium chloride and extracted with ethyl acetate. The organic phase is washed with a saturated aqueous solution of sodium chloride, dried over magnesium sulfate, filtered and the solvent evaporated off. 0.23 g of the title product is recovered after purification by chromatography on a silica column (eluent: hexane/ethyl acetate; 95:5).

Yield: 41.9%

$^1$H NMR (CDCl$_3$) δ: 2.64 (s, 1H); 7.42 (d, 1H); 7.61 (d, 1H); 10.09 (s, 1H)

IR (film) σ: 1710 cm$^{-1}$ (C=O)

EXAMPLE 19

Preparation of (4-aminomethyl-4-fluoropiperidin-1-yl)-(3-chloro-4-fluorophenyl)methanone (V-I)

Stage 1: (4-fluoro-4-hydroxymethylpiperidin-1-yl)-(3-chloro-4-fluorophenyl)methanone 11.9 g of (1-oxa-6-azaspiro[2.5]oct-6-yl)-(3-chloro-4-fluorophenyl)methanone (44.12 mmol) are dissolved in 20 ml of dichloromethane. 13 ml of HF-pyridine complex (441 mmol) are introduced into the solution cooled to 0° C. and maintained under nitrogen. The solution is stirred for 12 hours at room temperature and then the mixture is poured into ice-cold water. The medium is basified by addition of potassium carbonate and then extracted with chloroform. The organic phase is washed with a 1N aqueous solution of hydrochloric acid, dried over magnesium sulfate, filtered and concentrated under vacuum. The title product is purified by recrystallization from an ethanol/ethyl acetate mixture. 6.40 g of a white crystalline powder are obtained.

Yield: 50% m.p.: 188–90° C.

Analysis C$_{13}$H$_{14}$ClF$_2$NO$_2$:

Calc. %: C 53.90 H 4.87 Cl 12.24 N 4.83

Found: 54.08 4.86 12.28 4.70

$^1$H NMR (CDCl$_3$) δ: 1.35–2.15 (m, 4H); 1.63 (s, 1H (exchangeable)); 2.95–3.50 (m, 3H); 3.64 (d, 2H); 4.29–4.70 (m, 1H); 7.12–7.32 (m, 2H); 7.47 (dd, 1H)

IR (KBr) σ: 1612 cm$^{-1}$ (C=O); 3328 cm$^{-1}$ (O-H).

Stage 2: toluene-4-sulfonic acid 1-(3-chloro-4-fluorobenzoyl)-4-fluoropiperidin-4-yl-methyl Ester 4.87 g of para-toluenesulfonyl chloride (25.5 mmol) are slowly added to a solution of 6.70 g of (4-fluoro-4-hydroxymethylpiperidin-1-yl)-(3-chloro-4-fluorophenyl)methanone (23.12 mmol) in 40 ml of pyridine cooled to 0° C. and maintained under a nitrogen atmosphere. The mixture is stirred for 12 hours at room temperature and then it is poured into ice-cold water, extracted with chloroform and then the organic phase is washed with a 1N aqueous solution of hydrochloric acid. The organic phase is dried over magnesium sulfate, filtered and then concentrated under vacuum. The title product is purified by recrystallization from a dichloromethane/diisopropyl ether mixture. 7.73 g of a white crystalline powder are obtained.

Yield: 76% m.p.: 92° C.

$^1$H NMR (CDCl$_3$) δ: 1.35–1.95 (m, 4H); 2.43 (s, 3H); 2.95–3.90 (m, 2H); 3.60 (dd, 1H); 3.97 (d, 2H); 4.25–4.70 (m, 1H); 7.15 (t, 1H); 7.25 (m, 2H); 7.34 (d, 1H); 7.44 (dd, 1H); 7.76 (d, 2H).

Stage 3: 2-[1-(chloro-4-fluorobenzoyl)-4-fluoro-piperidin-4-yl-methyl]isoindole-1,3-dione A mixture of 5.42 g of toluene-4-sulfonic acid 1-(3-chloro-4-fluorobenzoyl)-4-fluoropiperidin-4-yl methyl ester (12.2 mmol) and 2.96 g of potassium phthalimide (16 mmol) in 70 ml of N,N-dimethylformamide is heated at 150° C. for 5 hours.

The mixture is poured into ice-cold water and then extracted with chloroform. After evaporation of the solvents under vacuum, the title product is isolated by chromatography on a silica column (eluent:chloroform/ethyl acetate; 90:10). 4.02 g of a white crystalline powder are obtained.

Yield: 79% m.p.: 133–34° C.

Analysis C$_{21}$H$_{17}$F$_2$ClN$_2$O$_3$:

Calc. %: C 60.22 H 4.09 Cl 18.46 N 6.69

Found: 60.12 3.97 8.51 6.71

$^1$H NMR (CDCl$_3$) δ: 1.90 (m, 4H); 3.25 (m, 2H); 3.65 (m, 1H); 3.90 (d, 2H); 4.55 (m, 1H); 7.12 (t, 1H); 7.27 (m, 1H); 7.48 (dd, 1H); 7.75 (m, 2H); 7.88 (m, 2H).

IR (KBr) σ: 1716 and 1776 cm$^{-1}$ (C=O).

Stage 4: (4-aminomethyl-4-fluoropiperidin-1-yl)-(3-chloro-4-fluorophenyl)methanone 0.10 g of 2-[1-(3-chloro-4-fluorobenzoyl)-4-fluoropiperidin-4-yl-methyl]isoindole-1,3-dione (0.238 mmol) and 0.50 ml of ethanolamine (8.28 mmol) are mixed and the solution obtained is heated at 55° C. under a nitrogen atmosphere for 2 hours. The mixture is poured into ice-cold water and then extracted with chloroform. The organic phase is washed with a saturated aqueous solution of sodium chloride, dried over magnesium sulfate, filtered and the solvent evaporated off. 0.06 g of the title product is obtained in the form of a colorless oil which is used in the next stage without further purification.

$^1$H NMR (CDCl$_3$) δ: 1.21–1.75 (m, 4H of which 2 exchangeable H); 1.90 (m, 2H); 2.79 (d, 2H); 3.22 (m, 2H); 3.62 (m, 1H); 4.49 (m, 1H); 7.14 (t, 1H); 7.25 (m, 1H) ; 7 44 (dd, 1H).

EXAMPLE 20

Preparation of (4-aminomethyl-4-fluoro-piperidin-1-yl)-(3,4-dichlorophenyl)-methanone (V-2)

By carrying out the procedure as in Example 19 but replacing in stage 1 the (1-oxa-6-azaspiro[2.5]oct-6-yl)-(3-chloro-4-fluorophenyl)methanone with (1-oxa-6-azaspiro[2.5]oct-6-yl)-(3,4-dichlorophenyl)methanone, in stage 2 the (4-fluoro-4-hydroxymethylpiperidin-1-yl)-(3-chloro-4-fluorophenyl)methanone with (4-fluoro-4-hydroxymethylpiperidin-1-yl)-(3,4-dichlorophenyl)-methanone, in stage 3 the toluene-4-sulfonic acid 1-(3-chloro-4-fluorobenzoyl)-4-fluoropiperidin-4-yl methyl ester with toluene-4-sulfonic acid 1-(3,4-dichloro-benzoyl)-4-fluoropiperidin-4-yl-methyl ester and in stage 4 the 2-[1-(3-chloro-4-fluorobenzoyl)-4-fluoro-piperidin-4-yl-methyl] isoindole-1,3-dione with 2-[1-(3,4-dichlorobenzoyl)-4-fluoropiperidin-4-ylmethyl]iso-indole-1,3-dione, the title compound is obtained in the form of a yellow oil.

$^1$H NMR (CDCl$_3$) δ: 1.24–1.80 (m, 4H of which 2 exchangeable H); 1.94 (m, 2H); 2.82 (d, 2H); 3.28 (m, 2H); 3.59 (m, 1H); 4.52 (m, 1H); 7.26 (m, 1H); 7.48 (m, 2H).

EXAMPLE 20a

Preparation of (4-aminomethyl-4-fluoropiperidin-1-yl)-(3-chloro-4-methylphenyl)methanone (V-3)

By carrying out the procedure as in Example 19 but using, as starting material, (1-oxa-6-azaspiro-[2.5]oct-6-yl)-(3-chloro-4-methylphenyl)methanone, the title compound is obtained in the form of a yellow oil.

$^1$H NMR (CDCl$_3$) δ: 1.23 (m, 2H); 1.59 (m, 2H); 1.95 (m, 2H); 2.40 (s, 2H); 2.87 (d, 2H); 3.14 (m, 1H); 3.37 (m, 1H); 3.60 (m, 1H); 4.56 (m, 1H); 7.21 (dd, 1H); 7.27 (d, 1H); 7.39 (d, 1H)

EXAMPLE 21

Preparation of (4-azidomethyl-4-fluoro-piperidin-1-yl)-(3-chloro-4-fluoro-phenyl)methanone (VI-1)

0.70 g of toluene-4-sulfonic acid 1-(3-chloro-4-fluorobenzoyl)-4-fluoropiperidin-4-yl-methyl ester (1.57 mmol), 0.308 g of sodium azide (4.70 mmol) and 0.20 g of tetrabutylammonium azide (0.70 mmol) are mixed in 3.50 ml of dimethyl sulfoxide. The mixture is heated at 110° C. under a nitrogen atmosphere for 20 hours. The reaction mixture is poured into ice-cold water and then extracted with ethyl acetate. The organic phase is washed with water and then with a saturated aqueous solution of sodium chloride, dried over magnesium sulfate, filtered and concentrated under vacuum. The title product is isolated by chromatography on a neutral alumina column (eluent: hexane/ethyl acetate; 70:30). 0.313 g of a yellow oil is obtained.

Yield: 63%

$^1$H NMR (CDCl$_3$) δ: 1.63 (m, 2H); 1.98 (m, 2H); 3.25 (m, 2H); 3.36 (d, 2H); 3.66 (m, 1H); 4.54 (m, 1H); 7.14–7.50 (m, 3H).

IR (film) σ: 1635 cm$^{-1}$ (C=O); 2102 cm$^{-1}$ (N$_3$).

EXAMPLE 22

Preparation of (4-azidomethyl-4-fluoro-piperidin-1-yl)-(3,4-dichlorophenyl)-methanone (VI-2)

In a manner similar to Example 21 but starting with toluene-4-sulfonic acid 1-(3,4-dichlorobenzoyl)-4-fluoropiperidin-4-yl-methyl ester in place of toluene-4-sulfonic acid 1-(3-chloro-4-fluorobenzoyl)-4-fluoropiperidin-4-yl-methyl ester, the title product is obtained in the form of a yellow oil.

$^1$H NMR (CDCl$_3$) δ: 1.55 (m, 2H); 1.96 (m, 2H); 3.20 (m, 2H); 3.33 (d, 2H); 3.60 (m, 1H); 4.54 (m, 1H); 7.20 (dd, 1H); 7.47 (m, 2H).

IR (film) σ: 1638 cm$^{-1}$ (C=O); 2102 cm$^{-1}$ (N$_3$).

EXAMPLE 23

Preparation of (3,4-dichlorophenyl)-(4-{[(6-fluoropyridin-2-ylmethyl)amino]-methyl}piperidin-1-yl)methanone (I-51)

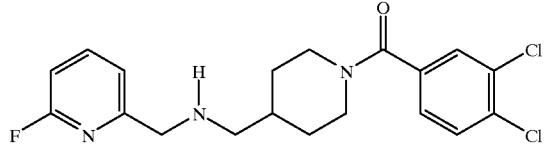

0.29 g of 6-fluoropyridine-2-carbaldehyde (2.31 mmol) and 0.264 g of piperidin-4-ylmethylamine (2.31 mmol) are mixed in 20 ml of benzene. The solution is heated under reflux under a nitrogen atmosphere for 2 hours with removal of the water formed continuously. The solvent is evaporated off and the residue is taken up in 2 ml of tetrahydrofuran. The solution obtained is cooled to 0° C., 0.50 ml of triethylamine (3.50 mmol) is added successively and then 0.469 g of 3,4-dichlorobenzoyl chloride (2.24 mmol) diluted in 1 ml of tetrahydrofuran is added dropwise. The mixture is stirred for 2 hours at room temperature. 10 ml of methanol are added followed, in portions, by 0.25 g of potassium borohydride (4.62 mmol). After 4 hours at room temperature, the solvents are evaporated off, the residue is taken up in water and extracted with chloroform. The organic phase is washed with water, dried over magnesium sulfate, filtered and concentrated under vacuum. The title product is isolated by chromatography on a silica column (eluent: chloroform/methanol; 95:5). 0.40 g of a yellow solid is obtained.

Yield: 40% m.p.: 78° C.

$^1$H NMR (CDCl$_3$) δ: 1.18 (m, 2H); 1.77 (m, 3H); 1.99 (s, 1H (exchangeable)); 2.52 (d, 2H); 2.86 (m, 2H); 3.66 (m, 1H); 3.82 (s, 2 H); 4.67 (m, 1H); 6.78 (dd, 1H); 7.22 (m, 2H); 7.46 (m, 2H); 7.72 (q, 1H).

EXAMPLE 24

Preparation of (4-{[(6-azetidin-1-yl-pyridin-2-yl-methyl)amino]methyl}-piperidin-1-yl)-3,4-dichlorophenyl)-methanone (I-17)

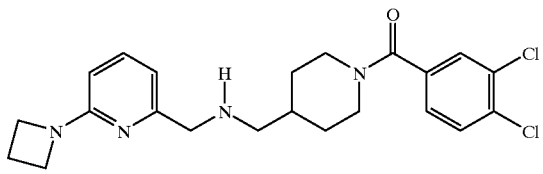

0.121 g of azetidine (3.15 mmol) is added to a solution of 0.70 g of (3,4-dichlorophenyl)-(4-{([(6-fluoropyridin-2-yl-methyl)amino]methyl}piperidin-1-yl)-methanone (1.77 mmol) in 10 ml of tetrahydrofuran. The solution is heated at 100° C. for 32 hours. The solvent is evaporated under vacuum and then the residue is taken up in water, and the mixture is extracted with chloroform. The organic phase is washed with water and then with a saturated solution of sodium chloride, dried over magnesium sulfate, filtered and concentrated under vacuum. The title product is isolated by chromatography on a silica column (eluent: chloroform/methanol; 90:10). 0.401 g of a yellow oil is obtained.

Yield: 52.3%

$^1$H NMR (CDCl$_3$) δ: 1.22 (m, 2H); 1.78 (m, 3H); 2.13 (s, 1H (exchangeable); 2.34 (m, 2H); 2.51 (d, 2H); 2.75 (m, 1H); 3.01 (m, 1H); 3.60 (m, 1H); 3.69 (s, 2H); 3.97 (t, 4H); 4.61 (m, 1H); 6.10 (d, 1H); 6.48 (d, 1H); 7.18 (dd, 1H), 7.34 (dd, 1H); 7.42 (m, 2H).

0.34 g of the title product (0.784 mmol) is dissolved in 1 ml of ethanol and then 0.067 g of oxalic acid (0.745 mmol) is added. After dissolution, the salt is precipitated by addition of ethyl acetate, filtered, washed with ethyl acetate and then dried at 50° C. under vacuum. 0.290 g of the oxalate of the title compound is obtained in the form of a white crystalline powder.

m.p.: 220–21° C.

Analysis C$_{24}$H$_{28}$Cl$_2$N$_4$O$_5$:

Calc. %: C 55.07 H 5.39 Cl 13.55 N 10.70

Found: 54.87 5.41 13.29 10.63

$^1$H NMR (DMSOd6) δ: 1.19 (m, 2H); 1.80 (m, 2H); 2.00 (m, 1H); 3.35 (m, 2H); 2.75 (m, 1H); 2.88 (d, 2H); 3.04 (m, 1H); 3.49 (m, 1H); 3.95 (t, 4H); 4.09 (s, 2H); 4.39 (m, 1H); 6.31 (d, 1H); 6.68 (d, 1H); 7.35 (dd, 1H); 7.53 (t, 1H); 7.65 (d, 1H); 7.70 (d, 1H).

IR (KBr) σ: 1632 and 1710 cm$^{-1}$ (C=O).

EXAMPLE 25

Preparation of (3-chloro-4-fluorophenyl)-(4-fluoro-4-{[(6-furan-2-yl-pyridin-2-yl-methyl)amino]methyl}-piperidin-1-yl)methanone (I-32)

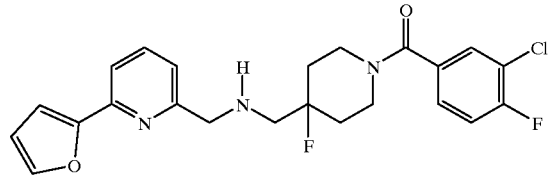

0.687 g of (4-aminomethyl-4-fluoropiperidin-1-yl)-(3-chloro-4-fluorophenyl)methanone (2.38 mmol) and 0.371 g of 6-furan-2-yl-pyridine-2-carbaldehyde (2.38 mmol) are mixed in 25 ml of toluene. The solution is heated under reflux under a nitrogen atmosphere for 2 hours, removing the water formed continuously. The toluene is evaporated off, the residue is taken up in 25 ml of methanol and then 0.257 g of potassium borohydride (4.51 mmol) is added in portions. The reaction mixture is stirred for 5 hours at room temperature and then the methanol is evaporated off. The residue is taken up in chloroform, the organic phase is washed with water and then with a saturated aqueous solution of sodium chloride, dried over magnesium sulfate, filtered and concentrated under vacuum. The title product is isolated by chromatography on a silica column (eluent: chloroform/methanol; 98:2). 0–65 g of a yellow oil is obtained.

Yield: 61.2%

$^1$H NMR (CDCl$_3$) δ: 1.40–2.20 (m, 5H of which 1 exchangeable H); 2.81 (d, 2H); 3.28 (m, 2H); 3.57 (m, 1H); 3.94 (s, 2H); 4.48 (m, 1H); 6.51 (q, 1H); 7.02 (d, 1H); 7.19 (m, 4H); 7.55 (m, 3H).

0.620 g of the title product (1.39 mmol) is dissolved in 20 ml of ethanol and then 0.160 g of fumaric acid (1.38 mmol) is added. The solution is concentrated, the salt is precipitated by addition of ethyl acetate, filtered, washed with ethyl acetate and then dried under vacuum at 50° C. 0.520 g of the fumarate of the title compound is obtained in the form of a white crystalline powder.

m.p.: 158° C.

Analysis C$_{27}$H$_{26}$ClF$_2$N$_3$O$_6$:

Calc. %: C 57.71 H 4.66 Cl 6.31 N 7.48

Found: 57.96 4.70 6.31 7.45

$^1$H NMR (DMSOd6) δ: 1.72 (m, 1H); 1.85 (m, 3H); 2.81 (d, 2H); 2.95–3.55 (m, 3H); 3.91 (s, 2H); 4.25 (m, 1H); 6.60 (s, 2H); 6.64 (q, 1H); 7.09 (d, 1H); 7.34 (d, 1H); 7.47 (m, 2H); 7.62 (m, 2H); 7.82 (t, 2H).

IR (KBr) σ: 1621 and 1701 cm$^{-1}$ (C=O).

EXAMPLE 26

Preparation of (3-chloro-4-fluoro-phenyl)-(4-fluoro-4-{[(6-dimethylaminopyridin-2-yl-methyl)amino]methyl}-piperidin-1-yl)methanone (I-13)

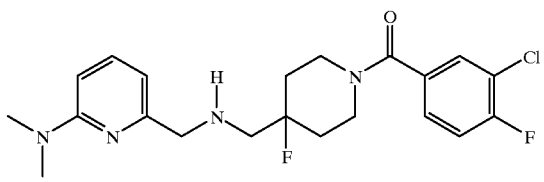

By carrying out the procedure as in Example 25 but replacing the 6-furan-2-yl-pyridine-2-carbaldehyde with 6-dimethylaminopyridine-2-carbaldehyde, the title compound is obtained in the form of a yellow oil after purification on a silica column (eluent:chloroform/methanol; 97:3).

Yield: 69.5%

$^1$H NMR (CDCl$_3$) δ: 1.57 (m, 1H); 1.73 (m, 1H); 2.00 (m, 2H); 2.15 (s, 1H (exchangeable); 2.75 (d, 2H); 3.04 (s, 6H); 3.25 (m, 2H); 3.55 (m, 1H); 3.72 (s, 2H); 4.62 (m, 1H); 6.34 (d, 1H); 6.43 (d, 1H); 7.14 (t, 1H); 7.27 (m, 1H); 7.35 (dd, 1H); 7.46 (dd, 1H).

0.650 g of the title product (1.53 mmol) is dissolved in 20 ml of ethanol and then 0.170 g of fumaric acid (1.46 mmol) is added. The solution is concentrated, the salt is precipitated by addition of ethyl acetate, filtered, washed with ethyl acetate and then dried under vacuum at 50° C. 0.560 g of the fumarate of the title compound is obtained in the form of a white crystalline powder.

m.p.: 159° C

Analysis C$_{25}$H$_{29}$ClF$_2$N$_4$O$_5$:

Calc. %: C 55.71 H 5.42 Cl 6.58 N 10.40

Found: 55.87 5.39 6.52 10.38

$^1$H NMR (DMSOd6) δ: 1.65 (m, 1H); 1.85 (m, 3H); 2.82 (d, 2H); 3.00 (s, 6H); 3.10–3.60 (m, 3H); 3.75 (s, 2H); 4.25 (m, 1H); 6.50 (d, 1H); 6.59 (d, 1H); 6.60 (s, 2H); 7.46 (m, 3H); 7.68 (dd, 1H).

IR (KBr) σ: 1637, 1686 and 1700 cm$^{-1}$ (C=O).

EXAMPLE 27

Preparation of (3,4-dichlorophenyl)-(4-fluoro-4-{[(6-dimethylaminopyridin-2-yl-methyl)amino]methyl}piperidin-1-yl)-methanone (I-14)

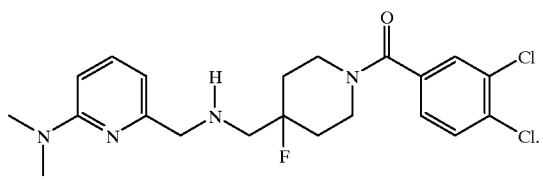

By carrying out the procedure as in Example 25 but replacing the 6-furan-2-yl-pyridine-2-carbaldehyde with 6-dimethylaminopyridine-2-carbaldehyde and the (4-aminomethyl-4-fluoropiperidin-1-yl)-(3-chloro-4-fluorophenyl)methanone with (4-aminomethyl-4-fluoropiperidin-1-yl)-(3,4-dichlorophenyl)methanone, the title compound is obtained in the form of a yellow oil after purification on a silica column (eluent:ethyl acetate).

Yield: 57.8%

$^1$H NMR (CDCl$_3$) δ: 1.40–1.85 (m, 2H); 2.02 (s, 1H (exchangeable)); 2.04 (m, 2H); 2.76 (d, 2H); 3.05 (s, 6H); 3.10–3.65 (m, 3H); 3.73 (s, 2H); 4.48 (m, 1H); 6.35 (d, 1H); 6.44 (d, 1H); 7.20 (dd, 1H); 7.36 (dd, 1H); 7.47 (m, 2H).

0.450 g of the title product (1.02 mmol) is dissolved in 10 ml of ethanol and then 0.115 g of fumaric acid (0.99 mmol) is added. The solution is concentrated, and the crystallization is initiated by addition of ethyl acetate. The precipitate is filtered, washed with ethyl acetate and then dried under vacuum at 50° C. 0.470 g of the fumarate of the title compound is obtained in the form of a white crystalline powder.

m.p.: 174° C.

Analysis C$_{25}$H$_{29}$Cl$_2$FN$_4$O$_5$:

Calc. %: C 54.06 H 5.26 Cl 12.77 N 10.09

Found: 53.82 5.34 12.61 9.83

$^1$H NMR (DMSOd6) δ: 1.71 (m, 1H); 1.83 (m, 1H); 2.79 (d, 2H); 2.99 (s, 6H); 3.05–3.50 (m, 3H); 3.72 (s, 2H); 4.23 (m, 1H); 6.48 (d, 1H); 6.56 (d, 1H); 6.58 (s, 2H); 7.37 (dd, 1H); 7.44 (dd, 1H); 7.69 (m, 2H).

IR (KBr) σ: 1636 and 1702 cm$^{-1}$ (C=0).

EXAMPLE 28

Preparation of (3-chloro-4-fluoro-phenyl)-(4-fluoro-4-{[(5-methyl-6-methylaminopyridin-2-ylmethyl)amino]-methyl}piperidin-1-yl)methanone (I-55)

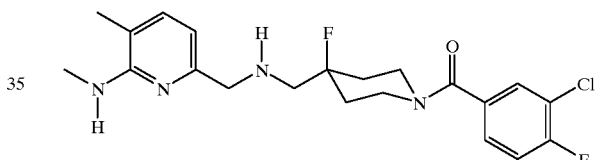

By carrying out the procedure as in Example 25 but replacing the 6-furan-2-yl-pyridine-2-carbaldehyde with 5-methyl-6-methylaminopyridine-2-carbaldehyde, the title compound is obtained in the form of a yellow oil after purification on a silica column (eluent:dichloromethane/methanol; 95:5).

Yield: 55.6%

$^1$H NMR (CDCl$_3$) δ: 1.60 (m, 2H); 1.98 (m, 6H); 2.72 (d, 2H); 2.95 (s, 3H); 3.11 (m, 1H); 3.32 (m, 1H); 3.51 (m, 1H); 3.68 (s, 2H); 4.08 (s, 1H); 4.44 (m, 1H); 6.38 (d, 1H); 7.10 (m, 2H); 7.21 (m, 1H); 7.42 (dd, 1H)

The salification of the title product with fumaric acid in ethanol gives 0.345 g of the fumarate of the title compound in the form of a white crystalline powder.

m.p.: 163–64° C.

Analysis C$_{25}$H$_{29}$ClF$_2$N$_4$O$_5$:

Calc. %: C 55.71 H 5.42 Cl 6.58 N 10.39

Found: 55.64 5.42 6.46 10.36

$^1$H NMR (DMSOd6) δ: 1.72 (m, 2H); 1.78 (m, 3H); 2.00 (s, 3H); 2.80 (d, 2H); 2.83 (s, 3H); 3.06 (m, 1H); 3.25 (m, 1H); 3.51 (m, 1H); 3.69 (s, 2H); 4.26 (m, 1H); 5.91 (d, 1H); 6.44 (d, 1H); 6.59 (s, 2H); 7.15 (d, 1H); 7.46 (m, 2H); 7.65 (dd, 1H)

IR (KBr) σ: 1638 and 1690 cm$^{-1}$

EXAMPLE 29

Preparation of (3-chloro-4-fluoro-phenyl)-(4-fluoro-4-{[(5-methyl-6-dimethylaminopyridin-2-yl-methyl)amino]-methyl}piperidin-1-yl)methanone (I-61)

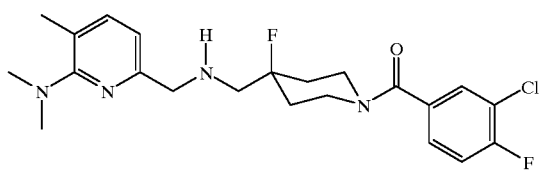

By carrying out the procedure as in Example 25 but replacing the furan-2-yl-pyridine-2-carbaldehyde with 5-methyl-6-dimethylaminopyridine-2-carbaldehyde and the reaction solvent (toluene) with benzene, the title compound is isolated by chromatography on a silica column (eluent: ethyl acetate/methanol; 98:2).

Yield: 66.7%

$^1$H NMR (CDCl$_3$) δ: 1.68 (m, 2H); 2.04 (m, 2H); 2.26 (s, 3H); 2.80 (d, 2H); 2.85 (s, 6H); 3.17 (m, 1H); 3.39 (m, 1H); 3.60 (m, 1H); 3.79 (s, 2H); 4.52 (m, 1H); 6.69 (d, 1H); 7.17 (t, 1H); 7.28 (m, 2H); 7.48 (d, 1H)

The salification of the title product with oxalic acid in ethanol gives 0.46 g of oxalate of the title compound in the form of a white crystalline powder.

m.p.: 205° C.

Analysis C$_{24}$H$_{29}$ClF$_2$N$_4$O$_5$:

Calc. %: C 54.70 H 5.55 Cl 6.73 N 10.63

Found: 54.62 5.55 6.76 10.48

$^1$H NMR (DMSOd6) δ: 1.75 (dt, 1H); 1.85 (m, 2H); 1.98 (m, 1H); 2.24 (s, 3H); 2.82 (s, 6H); 3.07 (m, 1H); 3.18 (d, 2H); 3.26 (m, 1H); 3.44 (m, 1H); 4.08 (s, 2H); 4.30 (m, 1H); 6.89 (d, 1H); 7.45 (m, 3H); 7.67 (dd, 1H)

IR (KBr) σ: 1636 and 1704 cm$^{-1}$

The compounds of general formula (I), which are obtained from the intermediates or from intermediates analogous to those of Examples 1 to 22, according to processes similar to those of Examples 23 to 29 and containing the desired substituents, are assembled in Table 1 below.

Derivatives of formula (I):

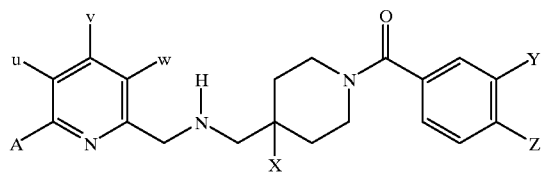

TABLE 1

| No. | A | u | v | w | x | y | z | SALT | m.p. ° C. |
|---|---|---|---|---|---|---|---|---|---|
| I-1 | pyrazol-N | H | H | H | H | Cl | Cl | maleate | 152–54 |
| I-2 | pyrazol-N | H | H | H | H | Cl | F | fumerate | 181–83 |
| I-3 | pyrazol-N | H | H | H | H | CH$_3$ | Cl | fumerate | 180–82 |
| I-4 | pyrazol-N | H | H | H | H | Cl | H | oxalate | 174–76 |
| I-5 | pyrazol-N | H | H | H | H | CH$_3$ | H | fumerate | 188–90 |
| I-6 | pyrazol-N | H | H | H | F | Cl | Cl | hemifumarate | 138–40 |
| I-7 | imidazol-N | H | H | H | H | Cl | Cl | maleate | 125–30 |

TABLE 1-continued
| No. | A | u | v | w | x | y | z | SALT | m.p. °C. |
|---|---|---|---|---|---|---|---|---|---|
| I-8 | 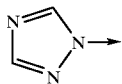 | H | H | H | H | Cl | Cl | fumerate | 168–70 |
| I-9 | 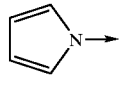 | H | H | H | H | Cl | Cl | hemifumarate | 174–76 |
| I-10 | 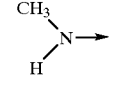 | H | H | H | H | Cl | Cl | maleate | 117–19 |
| I-11 | 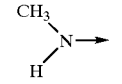 | H | H | H | F | Cl | Cl | fumarate | 167–68 |
| I-12 | 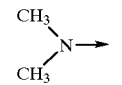 | H | H | H | H | Cl | Cl | fumarate | 175–77 |
| I-13 | 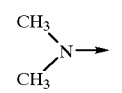 | H | H | H | F | Cl | F | See Example 26 | |
| I-14 | 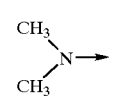 | H | H | H | F | Cl | Cl | See Example 27 | |
| I-15 | 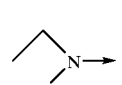 | H | H | H | F | Cl | Cl | oxalate | 203–05 |
| I-16 | 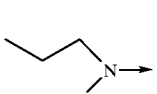 | H | H | H | H | Cl | Cl | oxalate | 186–88 |
| I-17 | 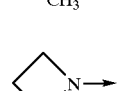 | H | H | H | H | Cl | Cl | See Example 24 | |
| I-18 | 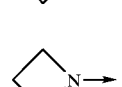 | H | H | H | F | Cl | Cl | oxalate | 215–17 |
| I-19 | 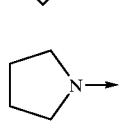 | H | H | H | H | Cl | Cl | oxalate | 203–05 |
| I-20 | Cl | H | H | H | H | Cl | Cl | fumarate | 174–76 |
| I-21 | 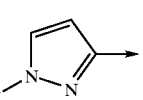 | H | H | H | H | Cl | Cl | oxalate | 149–51 |
| I-22 | 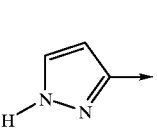 | H | H | H | F | Cl | Cl | oxalate | 150–52 |

TABLE 1-continued
| No. | A | u | v | w | x | y | z | SALT | m.p. °C. |
|---|---|---|---|---|---|---|---|---|---|
| I-23 | 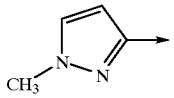 | H | H | H | F | Cl | Cl | oxalate | 186–88 |
| I-24 | 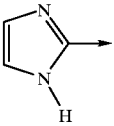 | H | H | H | H | Cl | Cl | fumarate | 206–08 |
| I-25 | 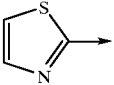 | H | H | H | H | Cl | Cl | fumarate | 187–89 |
| I-26 | 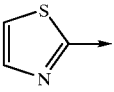 | H | H | H | F | Cl | Cl | hemifumarate | 146–48 |
| I-27 | 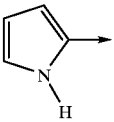 | H | H | H | H | Cl | Cl | oxalate | 209–11 |
| I-28 | 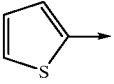 | H | H | H | H | Cl | Cl | oxalate | 208–10 |
| I-29 | 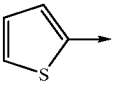 | H | H | H | F | Cl | Cl | hemifumarate | 172–74 |
| I-30 | 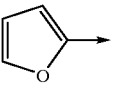 | H | H | H | H | Cl | Cl | hemifumarate | 178–80 |
| I-31 | 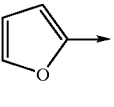 | H | H | H | F | Cl | Cl | fumarate | 157–59 |
| I-32 | 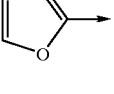 | H | H | H | F | Cl | F | See Example 25 | |
| I-33 | 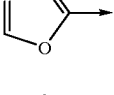 | H | H | H | H | Cl | Cl | oxalate | 189–91 |
| I-34 | 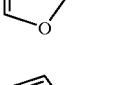 | H | H | H | F | Cl | Cl | oxalate | 182–84 |
| I-35 |  | H | H | H | F | Cl | Cl | hemifumarate | 139–141 |

TABLE 1-continued

| No. | A | u | v | w | x | y | z | SALT | m.p. ° C. |
|---|---|---|---|---|---|---|---|---|---|
| I-36 | 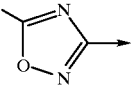 | H | H | H | H | Cl | Cl | fumarate | 164–66 |
| I-37 | CH$_3$ | H | H | H | H | Cl | Cl | fumarate | 156–58 |
| I-38 |  | H | H | H | H | Cl | Cl | fumarate | 148–50 |
| I-39 |  | H | H | H | F | Cl | Cl | fumarate | 161–63 |
| I-40 | FCH$_2$ | H | H | H | F | Cl | Cl | fumarate | 159–61 |
| I-41 | F$_2$CH | H | H | H | H | Cl | Cl | fumarate | 160–62 |
| I-42 | F$_2$CH | H | H | H | F | Cl | Cl | fumarate | 152–54 |
| I-43 |  | H | H | H | F | Cl | Cl | fumarate | 134–36 |
| I-44 |  | H | H | H | H | Cl | Cl | maleate | 135–37 |
| I-45 |  | H | H | H | H | Cl | Cl | fumarate | 142–44 |
| I-46 | CH$_3$O | H | H | H | H | Cl | Cl | maleate | 150–52 |
| I-47 | CH$_3$O | H | H | H | F | Cl | Cl | fumarate | 139–41 |
| I-48 |  | H | H | H | F | Cl | Cl | fumarate | 144–46 |
| I-49 | 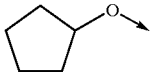 | H | H | H | H | Cl | Cl | fumarate | 168–70 |
| I-50 | CH$_3$S | H | H | H | H | Cl | Cl | oxalate | 142–44 |
| I-51 | F | H | H | H | H | Cl | Cl | oxalate | 182–84 |
| I-52 | F | H | H | H | F | Cl | Cl | fumarate | 142–44 |
| I-53 | H | H | H | F | H | Cl | Cl | fumarate | 156–58 |
| I-54 | H | H | Cl | H | H | Cl | Cl | maleate | 150–52 |
| I-55 |  | CH3 | H | H | F | Cl | F | See Example 28 | |
| I-56 |  | H | H | H | F | Cl | F | oxalate | 199–201 |
| I-57 | 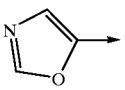 | H | H | H | F | Cl | F | Fumarate | 145–47 |

TABLE 1-continued

| No. | A | u | v | w | x | y | z | SALT | m.p. ° C. |
|---|---|---|---|---|---|---|---|---|---|
| I-58 | CH₃CH₂-NH- | H | H | H | F | Cl | F | Oxalate | 174–75 |
| I-59 | (CH₃)(H)N- | H | H | H | F | Cl | F | Fumarate | 164–65 |
| I-60 | (CH₃)₂N- | H | H | H | F | Cl | CH₃ | Fumarate | 167–68 |
| I-61 | (CH₃)₂N- | CH₃ | H | H | F | Cl | F | See Example 29 | |
| I-62 | 1H-pyrazol-3-yl | H | H | H | F | Cl | F | Oxalate | 178–79 |
| I-63 | (CH₃)₂N- | H | H | CH₃ | F | Cl | Cl | Oxalate | 169–71 |
| I-64 | pyrazol-1-yl | H | H | H | F | Cl | F | Fumarate | 174–75 |
| I-65 | H | CH₃ | H | H | F | Cl | Cl | Fumarate | 163–64 |
| I-66 | H | CH₃ | H | H | F | Cl | F | Fumarate | 156–58 |
| I-67 | pyrrolidin-1-yl | H | H | H | F | Cl | F | Oxalate | 198–99 |
| I-68 | (CH₃)₂N- | H | CH₃ | H | F | Cl | F | Fumarate | 140–42 |
| I-69 | Cl | CH₃ | H | H | F | Cl | F | Fumarate | 173–75 |
| I-70 | pyrazol-1-yl | CH₃ | H | H | F | Cl | F | Fumarate | 172–73 |
| I-71 | 1H-pyrazol-3-yl | CH₃ | H | H | F | Cl | H | Fumarate hemi-hydrate | 173–74 |

PHARMACOLOGICAL STUDY OF THE COMPOUNDS OF THE INVENTION

1-Measurement of the affinity of the compounds of the invention for the 5-HT1A receptors Protocol The in vitro affinity of the compounds of the invention for the 5-HT1A receptors was determined by measuring the displacement of ($^3$H)8-OH-DPAT (TRK 850; 160–240 Ci/mmol).

The study of binding to the 5-HT$_{1A}$ receptor was carried out as described by Sleight and Peroutka (Naunyn-Schmiedeberg's Arch. Pharmaco. 1991, 343, 106–16). For these experiments, rat cerebral cortices are used. After thawing the brain in 50 mmol Tris-HCl buffer, pH=7.40 at 25° C., the cerebral cortex is removed and homogenized in 20 volumes of buffer maintained at 4° C. The homogenate is centrifuged at 39,000 g for 10 minutes, the centrifugation pellet is suspended in the same volume of buffer and again centrifuged. After suspending again under the same conditions, the homogenate is incubated for 10 minutes at 37° C. and then centrifuged again. The final pellet is suspended in cold 50 mmol Tris-HCl reaction buffer, pH=7.40 at 25° C. containing 10 mmol of pargyline, 4 mmol of $CaCl_2$ and 0.10% of ascorbic acid. The final concentration of tissue in the incubation medium is 10 mg/tube.

The reaction tubes contain 0.10 ml of ($^3$H)8-OH-DPAT (0.20 mmol final), 0.10 ml of product to be tested 6–7 concentrations and 0.80 ml of tissue. Nonspecific binding is defined using 10 mmol of 5-HT. The reaction tubes are incubated at 23° C. for 30 minutes and then their content is rapidly filtered under vacuum on Whatman GF/B filters, the tubes are rinsed twice with 5 ml of 50 mmol Tris-HCl buffer, pH=7.4 at 25° C. The radioactivity collected on the filter is analyzed by liquid scintillation by adding 4 ml of scintillation fluid (Emulsifier Safe, Packard). All the experiments are carried out in triplicate.

2-Measurement of the affinity of the compounds of the invention for the $D_2$ receptors Protocol The in vitro affinity of the compounds of the invention for the $D_2$ dopaminergic receptors was determined by measuring the displacement of ($^3$H) YM-09151-2 (NET-1004 70–87 Ci/mmol). The study of binding to the $D_2$ receptor is carried out as described by Niznik (Naunyn-Schmiedeberg's Arch. Pharmacol. Methods, 1985, 329, 333–38). For these experiments, rat striatum is used. After thawing the brain in 50 mmol Tris-HCl buffer, pH=7.40 at 25° C., the striatum is collected and homogenized in 40 volumes of buffer maintained at 4° C. The homogenate is centrifuged at 20,000 g for 10 minutes, the centrifugation pellet is suspended in the same volume of buffer and again centrifuged. The final pellet is suspended in cold 50 mmol Tris-HCl reaction buffer, pH=7.40 at 25° C. containing 120 mmol of NaCl and 5 mmol of KCl. The final concentration of tissue in the incubation medium is 2 mg/tube. The reaction tubes contain 0.20 ml of [$^3$H]YM-09151-2 (0.05 mmol final), 0.20 ml of product to be tested 6–7 concentrations and 1.60 ml of tissue. Nonspecific binding is defined using 1 mmol of (+)-Butaclamol. The reaction tubes are incubated at 23° C. for 60 minutes and then their content is rapidly filtered under vacuum on Whatman GF/B filters, the tubes are rinsed twice with 5 ml of 50 mmol Tris-HCl buffer, pH=7.40 at 25° C. The radioactivity collected on the filter is analyzed by liquid scintillation by adding 4 ml of scintillation fluid (Emulsifier Safe, Packard). All the experiments are carried out in triplicate.

Results

The inhibition constants (Ki) of the products of the invention are estimated from displacement experiments using the nonlinear regression program RADLIG version 4 from EBDA (Equilibrium Binding Data Analysis) (Biosoft, Cambridge, UK, McPherson, 1985). The dissociation constants of the radioactive ligands used in the calculations are 0.31 mmol for ($^3$H)8-OH-DPAT and 0.036 mmol for ($^3$H) YM-09151-2. The pKi (-logKi) values are given in the form of the mean ±SEM of at least 3 experiments. Table 2 gives, by way of example, the pKi values (D2) as well as the 5-HT1A/D2 selectivity for several compounds of the invention, compared with Buspirone and with 8-OH-DPAT chosen as reference products.

TABLE 2

| Compound No. | pKi 5-$HT_{1A}$ | pKi $D_2$ | 5-$HT_{1A}$/$D_2$ Selectivity | LLR p.o (60 minutes) $ED_{50}$ mg/Kg |
|---|---|---|---|---|
| I-55 | 10.12 | 5.89 | 16982 | 0.08 |
| I-13 | 9.92 | 6.56 | 2291 | 0.31 |
| I-56 | 9.86 | 5.99 | 7414 | 0.08 |
| I-58 | 9.73 | 6.63 | 1259 | 0.31 |
| I-59 | 9.69 | 5.99 | 5011 | 0.31 |
| I-11 | 9.67 | 6.40 | 1862 | 0.31 |
| I-14 | 9.61 | 6.48 | 1349 | 0.31 |
| I-32 | 9.55 | 5.65 | 7942 | 0.31 |
| I-61 | 9.50 | 6.22 | 1906 | 0.08 |
| I-62 | 9.34 | 5.12 | 16594 | 0.31 |
| I-65 | 9.24 | <5 | >10000 | 0.31 |
| 8-OH-DPAT | 8.85 | 6.26 | 389 | 5 |
| Buspirone | 7.65 | 7.49 | 1.5 | 20 |

The compounds of general formula (I) are therefore very potent ligands for the 5-$HT_{1A}$ receptors and are found to be very selective toward the $D_2$ receptors.

3-Evaluation of the agonist activity of the 5-$HT_{1A}$ receptors of the compounds of the invention in vivo Protocol Sprague Dawley male rats (ICO: OFAD [IOPS], Iffa Credo, France) weighing 160–180 g on their arrival and 180–200 g at the beginning of the tests are used. The animals are quarantined for 4 to 8 days with free access to standard laboratory food before their use in the experiments. Animals are housed individually in plastic cages on a support, (28 cm×21 cm×18 cm) with a floor having a wire mesh covering (RC Iffa Credo), 24 hours before the tests. Water filtered on 0.22 μm is available ad libitum by means of an automatic dispenser. The quarantine area and the experimentation laboratory are air-conditioned (temperature: 22±1° C.; relative humidity: 55±5%) and illuminated from 07:00 to 19:00. All the rats are treated in accordance with laboratory animal ethics (Guide for the Care and Use of Laboratory Animals, U.S. Department of Agriculture. Public Health Service. National Institutes of Health publication No. 85–23, Revised 1985), and the protocol (No. 15) is carried out in accordance with the recommendations of the local ethics committee on animal research.

The methods used are essentially identical to those described previously (Drug. Dev. Res. 1992, 26, 21–48; Eur. J. Pharmacol. 1995, 281, 219–28).

The behavior of the animal is observed for a period of 10 minutes each, centred on t60 minutes, after administration by the oral route. Four animals are observed individually during the 10 minute period (from t55 to t65); the 4 rats are observed in turn, every 15 seconds, duration of observation 10 seconds per animal. During each of these observation periods, the presence (1) or absence (0) of lower lip retraction (LLR) in the animal is noted. Lower lip retraction is considered to exist if the animal exhibits uninterrupted signs for at least 3 seconds. This cycle is repeated 10 times over a period of 10 minutes; thus, the frequency of a behavior may vary from 0 to 10 for each observation period. Each day, two animals from each group receive the same dose of the same product.

The products are dissolved in distilled water or suspended in an aqueous solution of Tween 80 (2 drops/10 ml of distilled water). The products are administered in a volume of 10 ml/kg and the doses are expressed in basal weight. The order of administration of the products and of the doses is randomized.

Results

Table 2 gives, by way of example, the active doses ($ED_{50}$) for some derivatives of the invention compared with Buspirone and with 8-OH-DPAT.

The results of the tests therefore show that some compounds of general formula (I) possess an agonist activity on the 5-HT$_{1A}$ receptors, after oral administration in rats, which is much higher than that for the reference products.

We claim:

1. A compound selected from Pyridin-2-yl-methylamines of formula (I):

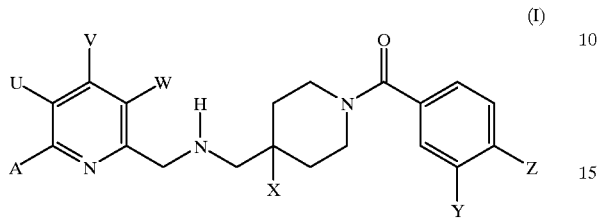

in which:
- u represents a hydrogen atom or a methyl radical with the proviso that when u is a methyl radical then v and w each represent a hydrogen atom;
- v represents a hydrogen atom or a chlorine atom or a methyl radical with the proviso that when v represents a chlorine atom or a methyl radical then u and w each represent a hydrogen atom;
- w represents a hydrogen atom or a fluorine atom or a methyl radical with the proviso that when w represents a fluorine atom or a methyl radical then u and v each represent a hydrogen atom;
- x represents a hydrogen atom or a fluorine atom;
- y represents a chlorine atom or a methyl radical;
- z represents a hydrogen atom or a fluorine atom or a chlorine atom or a methyl radical;
- A represents:
  - a hydrogen atom or a fluorine atom or a chlorine atom;
  - a C$_1$–C$_5$ alkyl radical, i.e. a straight or branched chain saturated aliphatic hydrocarbon radical containing 1 to 5 carbon atoms;
  - a fluoroalkyl radical
  - a cyclopropyl or cyclobutyl or cyclopentyl radical;
  - a substituted or unsubstituted 5-membered aromatic heterocyclic group containing 1, 2, 3 or 4 heteroatoms selected from nitrogen, oxygen and sulfur without, more than one oxygen and/or sulfur atom being present in the heterocycle A,
  - the aromatic heterocycles being selected from the group consisting of:
    - furan-2-yl, (O.CH:CH.CH:C—),
    - furan-3-yl, (CH:CH.O.CH:C—),
    - 1H-pyrrol-2-yl, (NH.CH:CH.CH:C—),
    - 1H-pyrrol-3-yl, (CH:CH.NH.CH:C—),
    - 1-methyl-pyrrol-2-yl, N(CCH$_3$).CH:CHCH:C—),
    - 1-methyl-pyrrol-3-yl, (CH:CH.N(C$_3$).CH:C—) or
    - thiophen-2-yl, (S.CH:CH.CH:C—),
    - thiophen-3-yl, (CH:CH.S.CH:C—),
    - pyrazol-yl, (N:CH.CH:CH.N—),
    - 1H-pyrazol-3-yl, (CH:CH.N:C—),
    - 1H-pyrazol-4-yl, (CH:N.NH.CH:C—),
    - 1-methyl-pyrazol-3-yl, (CH:CH.N(CH$_3$).N:C—),
    - imidazol-1-yl, (CH:N.CH:CH.N—),
    - 1H-imidazol-2-yl, (NH-CH:CH.N:C—),
    - 1H-imidazol-4-yl, (N:CH.NH.CH:C—),
    - oxazol-2-yl, (O.CH:CH.N:C—),
    - oxazol-4-yl, (N:CH.O.CH:C—),
    - oxazol-5-yl, (O.CH:N.CH:C—),
    - isoxazol-5-yl, (O.N:CH.CH:C—),
    - isoxazol-4-yl, (CH:N.O.CH:C—),
    - isoxazol-3-yl, (CH:CH.O.N:C—),
    - thiazol-2-yl, (S.CH:CH.N:C—),
    - thiazol-4-yl, (N:CH.S.CH.C—),
    - thiazol-5-yl, (S.CH:N.CH:C—),
    - isothiazol-5-yl, (S.N:CH.CH:C—),
    - isothiazol-4-yl, (CH:N.S.CH:C—),
    - isothiazol-3-yl, (CH:CH.S.SN:C—),
    - [1,2,4]triazol-1-yl, (CH:N.CH;N.N—),
    - 1H-[1,2,4]triazol-3-yl, (N:CH.NH.N:C—),
    - [1,2,4]oxadiazol-3-yl, (N:CH.O.N:C—),
    - [1,2,4]oxadiazol-5-yl, (O.N:CH.N:C—),
    - 5-methyl-[1,2,4]oxadiazol-3-yl, (N:C(CH$_3$).O.N:C—) and
    - 1H-tetrazol-5-yl, (NH.N:N.N:C—):
  - an alkoxy (R$_1$O) or alkylthio (R$_1$S—) group in which the R$_1$ radical represents:
    - a C$_1$–C$_5$ alkyl radical as defined above,
    - a monofluoromethyl or trifluoromethyl radical,
    - a cyclopropyl or cyclobutyl or cyclopentyl radical;
  - an amino group

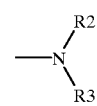

in which R$_2$ and R$_3$, which are identical or different, represent hydrogen, or a C$_1$–C$_5$ alkyl radical as defined above or a cyclopropyl or cyclobutyl radical or a trifluoromethyl radical;
  - a saturated cyclic amino group

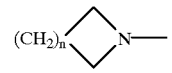

in which n is 1 or 2;
  - an alkoxycarbonyl group; and
- an addition salt thereof with a pharmaceutically-acceptable inorganic acid or organic acid.

2. A compound of the group consisting of:
- (3,4-Dichlorophenyl)-(4-{[(6-pyrazol-1-yl-pyridin-2-ylmethyl)amino]methyl}piperidin-1-yl)methanone,
- (3-Chloro-4-fluorophenyl)-(4-{[(6-pyrazol-1-yl-pyridin-2-ylmethyl)amino]methyl}piperidin-1-yl)methanone,
- (4-Chloro-3-methylphenyl)-(4-{[(6-pyrazol-1-yl-pyridin-2-ylmethyl)amino]methyl}piperidin-1-yl)methanone,
- (3-Chlorophenyl)-(4-{[(6-pyrazol-1-yl-pyridin-2-ylmethyl)amino]methyl}piperidin-1-yl)methanone,
- (4-{[(6-Pyrazol-1-yl-pyridin-2-ylmethyl)amino]methyl}-piperidin-1-yl)-m-tolylmethanone,
- (3,4-Dichlorophenyl)-(4-fluoro-4-{[(6-pyrazol-1-yl-pyridin-2-ylmethyl)amino]methyl}piperidin-1-yl) methanone,
- (3,4-Dichlorophenyl)-(4-{[(6-imidazol-1-yl-pyridin-2-ylmethyl)amino]methyl}piperidin-1-yl)methanone,
- (3,4-Dichlorophenyl)-(4-{([(6-[1,2,4]triazol-1-yl-pyridin-2-ylmethyl)amino]methyl}piperidin-1-yl) methanone,
- (3,4-Dichlorophenyl)-(4-{[(6-pyrrol-1-yl-pyridin-2-ylmethyl)amino]methyl}piperidin-1-yl)methanone, (3,4-Dichlorophenyl)-(4-{[(6-methylaminopyridin-2-ylmethyl)amino]methyl}piperidin-1-yl)methanone (3,4-Dichlorophenyl)-(4-fluoro-4-{[(6-methylaminopyridin-2-ylmethyl)amino]methyl}piperidin-1-yl)methanone, (3,4-Dichlorophenyl)-(4-{[(6-dimethylaminopyridin-2-ylmethyl)amino]methyl}piperidin-1-yl)methanone, (3-Chloro-4-fluorophenyl)-(4-{[(6-dimethylaminopyridin-2-ylmethyl)amino]methyl}-4-fluoropiperidin-1yl)methanone, (3,4-Dichlorophenyl)-(4-{[(6-dimethylaminopyridin-2-ylmethyl)amino]methyl}-4-fluoropiperidin-1-yl)methanone, (3,4-Dichlorophenyl)-[4-{(6-ethylmethylamino)pyridin-2-ylmethyl]amino}methyl)-4-fluoropiperidin-1-yl)methanone, (3,4-Dichlorophenyl)-[4-{[(6-(methylpropylamino)-pyridin-2-ylmethyl]amino methyl)piperidin-1-yl)-methanone, (4-{[(6-Azetidin-1-yl-pyridin-2-ylmethyl)amino]-methyl}piperidin-1-yl)-(3,4-dichlorophenyl)methanone, (4-{[6-Azetidin-1-yl -pyridin-2-ylmethyl)amino]methyl}-4-fluoropiperidin-1-yl)-(3,4-dichlorophenyl)methanone, (4-{[(6-Cyclopentylpyridin-2-ylmethyl)amino]methyl}-piperidin-1-yl)-(3,4-dichlorophenyl)methanone, (4-{[(6-Chloropyridin-2-ylmethyl)amino]methyl}-piperidin-1-yl)-(3,4-dichlorophenyl)methanone, (3,4-Dichlorophenyl)-[4-({[6-(1H-pyrazol-3-yl)pyridin-2-ylmethyl]amino}methyl)piperidin-1-yl]methanone, (3,4-Dichlorophenyl)-[4-[fluoro-4-({[6-(1H-pyrazol-3-yl)pyridin-2-ylmethyl]amino}methyl)piperidin-1-yl]methanone, (3,4-Dichlorophenyl)-[4-fluoro-4-({[6-(1-methylpyrazol-3-yl)pyridin-2-ylmethyl]amino}methyl)piperidin-1-yl]methanone, (3,4-Dichlorophenyl)-[4-({[6-(1-imidazol-2-yl)pyridin-2-ylmethyl]amino}methyl)piperidin-1-yl]methanone, (3,4-Dichlorophenyl)-(4-{[(6-thiazol-2-ylpyridin-2-ylmethyl)amino]methyl}piperidin-1-yl)methanone, (3,4-Dichlorophenyl)-(4-fluoro-4-{[(6-thiazol-2-yl-pyridin-2-ylmethyl)amino]methyl}piperidin-1-yl)methanone, (3,4-Dichlorophenyl)-[4-({[6-(1H-pyrrol-2-yl)pyridin-2ylmethyl]amino}methyl)piperidin-1-yl]methanone, (3,4-Dichlorophenyl)-(4-{[(6-thiophen-2-yl-pyridin-2-ylmethyl)amino]methyl}piperidin-1-yl)methanone, (3,4-Dichlorophenyl)-(4-fluoro-4-{[(6-thiophen-2-yl-pyridin-2-ylmethyl)amino]methyl}piperidin-1-yl]methanone, (3,4-Dichlorophenyl)-(4-{[(6-furan-2-yl-pyridin-2-ylmethyl)amino]methyl}piperidin-1-yl)methanone, (3,4-Dichlorophenyl)-(4-fluoro-4-{[(6-furan-2-yl-pyridin-2-ylmethyl)amino]methyl}piperidin-1-yl)methanone, (3-Chloro-4-fluorophenyl)-(4-fluoro-4-{[(6-furan-2-yl-pyridin-2-ylmethyl)amino]methyl}piperidin-1-yl]methanone, (3,4-Dichlorophenyl)-(4-{[(6-oxazol-5-yl-pyridin-2-ylmethyl)amino]methyl}piperidin-1-yl)methanone, (3,4-Dichlorophenyl)-(4-fluoro-4-{[(6-oxazol-5-yl-pyridin-2-ylmethyl)amino]methyl}piperidin-1-yl)methanone, (3,4-Dichlorophenyl)-(4-fluoro-4-{[(6-furan-3-yl-pyridin-2-ylmethyl)amino]methyl}piperidin-1-yl]methanone, (3,4-Dichlorophenyl)-[4-({[6-(5-methyl-[1,2,4]oxadiazol-3-yl)pyridin-2-ylmethyl]amino}methyl)-piperidin-1-yl)methanone, (3,4-Dichlorophenyl)-(4-{[(6-methylpyridin-2-ylmethyl)-amino]methyl}piperidin-1-yl)methanone, (3,4-Dichlorophenyl)-(4-{[(6-isopropylpyridin-2-ylmethyl)amino]methyl}piperidin-1-yl)methanone, (3,4-Dichlorophenyl)-(4-{[(6-cyclopropylpyridin-2-ylmethyl)amino]methyl}-4-fluoropiperidin-1-yl)methanone, (3,4-Dichlorophenyl)-(4-fluoro-4-{[(6-fluoromethyl-pyridin-2-ylmethyl)amino]methyl}piperidin-1-yl)-methanone, (3,4-Dichlorophenyl)-(4-{[(6-difluoromethylpyridin-2-ylmethyl)amino]methyl}piperidin-1-yl]methanone, (3,4-Dichlorophenyl)-(4-{[(6-difluoromethylpyridin-2-ylmethyl)amino]methyl}-4-fluoropiperidin-1-yl)methanone, (3,4-Dichlorophenyl)-[4-fluoro-4-({[6-(1-fluoroethyl)pyridin-2-ylmethyl]amino}methyl)piperidin-1-yl)methanone, 6-({[1-(3,4-Dichlorobenzoyl)piperidin-4-ylmethyl]-amino}methyl)pyridine-2-carboxylic acid methyl ester 6-({[1-(3,4-Dichlorobenzoyl)piperidin-4-ylmethyl]amino}methyl)pyridine-2-carboxylic acid ethyl ester, (3,4-Dichlorophenyl)-(4-{[(6-methoxypyridin-2-ylmethyl)amino]methyl}piperidin-1-yl)methanone, (3,4-Dichlorophenyl)-(4-fluoro-4-{[(6-methoxypyridin-2-ylmethyl)amino]methyl}piperidin-1-yl)methanone, (3,4-Dichlorophenyl)-(4-fluoro-4{[(6-isopropyloxypyridin-2-ylmethyl)amino)methyl}piperidin-1-yl)methanone, (4-{[(6-Cyclopentyloxypyridin-2-ylmethyl)amino]methyl}-piperidin-1-yl)-(3,4-dichlorophenyl)methanone, (3,4-Dichlorophenyl)-(4-{[(6-methylsulfanylpyridin-2-ylmethyl)amino]methyl}piperidin-1-yl)methanone, (3,4-Dichlorophenyl)-(4-{[(6-fluoropyridin-2-ylmethyl)amino]methyl}piperidin-1-yl)methanone, (3,4-Dichlorophenyl)-(4-fluoro-4-{[(6-fluoropyridin-2-ylmethyl)amino]methyl}piperidin-1-yl)methanone, (3,4-Dichlorophenyl)-(4-fluoro-{[(3-fluoropyridin-2-ylmethyl)amino]methyl}piperidin-1-yl)methanone, (4-{[(4-Chloropyridin-2-ylmethyl)amino]methyl}-piperidin-1-yl)-(3,4-dichlorophenyl)methanone, (3-Chloro-4-fluorophenyl)-(4-fluoro-4-{[(5-methyl-6-furan-2-yl-pyridin-2-ylmethyl)amino]methyl}piperidin-1-yl)methanone, (3-Chloro-4-fluorophenyl)-([4-fluoro-4-({[5-methyl-6-(1H-pyrazol-3-yl)-2-yl-pyridin-2-ylmethyl]amino}-methyl)piperidin-1-yl)methanone, (3-Chloro-4-fluorophenyl)-(4-fluoro-4-{[(5-methyl-6-methylaminopyridin-2-ylmethyl)amino]methyl}piperidin-1-yl)methanone, (4-{[(6-Azetidin-1-ylpyridin-2-ylmethyl)amino]methyl}-4-fluoropiperidin-1-yl)-(3-chloro-4-fluorophenyl)methanone, (3-Chloro-4-fluorophenyl)-(4-fluoro-4-{[(6-oxazol-5-yl-pyridin-2-ylmethyl)amino]methyl}piperidin-1-yl)methanone, (3-Chloro-4-fluorophenyl)-(4-fluoro-4-{[(6-ethylaminopyridin-2-ylmethyl)amino]methyl}piperidin-1-yl)methanone, (3-Chloro-4-fluorophenyl)-(4-fluoro-4-{[(6-methylaminopyridin-2-ylmethyl)amino]methyl}piperidin-1-yl)methanone, (3-Chloro-4-methylphenyl)-(4-fluoro-4-{[(6-dimethylaminopyridin-2-ylmethyl)amino]methyl}piperidin-1-yl)methanone, (3-Chloro-4-fluorophenyl)-(4-fluoro-4-{[(5-methyl-6-dimethylaminopyridin-2-ylmethyl)amino]methyl}piperidin-1-yl)methanone, (3-Chloro-4-fluorophenyl)-[4-fluoro-4-({[6-(1H-pyrazol-3-yl)pyridin-2-ylmethyl]amino}methyl)piperidin-1-yl]methanone, (3,4-Dichlorophenyl)-(4-fluoro-4-{[(3-methyl-6-dimethylaminopyridin-2-ylmethyl)amino]methyl}piperidin-1-yl)methanone, (3-Chloro-4-fluorophenyl)-(4-fluoro-4-{[(6-pyrazol-1-yl-pyridin-2-ylmethyl)amino]methyl}piperidin-1-yl)methanone, (3,4-Dichlorophenyl)-(4-fluoro-4-({[(5-methylpyridin-2-ylmethyl)amino]methyl}piperidin-1-yl)methanone, (3-Chloro-4-fluorophenyl)-(4-fluoro-4-{[(5-methylpyridin-2-ylmethyl)amino]methyl}piperidin-1-yl)methanone, (3-Chloro-4-fluorophenyl)-(4-fluoro-4-{[(6-diethylaminopyridin-2-ylmethyl)amino]methyl}piperidin-1-yl)methanone, (3-Chloro-4-fluoromethyl)-(4-fluoro-4-{[(5-methyl-6-chloropyridin-2-ylmethyl)amino]methyl}piperidin-1-yl)methanone, (3-Chloro-4-fluorophenyl)-(4-fluoro-4-{[(4-methyl-6-dimethylaminopyridin-2-ylmethyl)amino]methyl}piperidin-1-yl)methanone, (3-Chloro-4-fluorophenyl)-(4-fluoro-4-{[(5-methyl-6-pyrazol-1-yl-pyridin-2-ylmethyl)amino]methyl}piperidin-1-yl)methanone, and (3-Chlorophenyl)(4-fluoro-4-{[(6-dimethylaminopyridin-2-ylmethyl)amino]methyl}piperidin-1-yl)methanone, and pharmaceutically-acceptable acid addition salts of any of the foregoing.

3. Process for preparing a compound of claim 1 or 2, wherein an aldehyde of formula (IV) is reacted with an amine of formula (v) in a reducing medium:

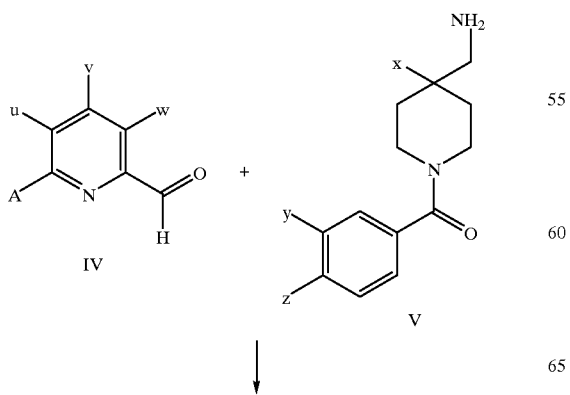

wherein: A, u, v, w, x, y and z are as defined in claim 1.

4. Process for preparing a compound of claim 1 or 2, wherein an aldehyde of formula (IV) is reacted with an azido compound of formula (VI) in the presence of an aryl or alkylphosphine in a reducing medium:

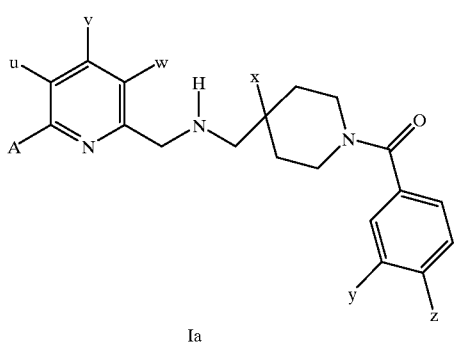

wherein: A, u, v, w, x, y and z are as defined in claim 1.

5. Process for preparing compound (Ib), wherein an aldehyde of formula (IV) is reacted successively with piperidin-4-yl-methylamine, an acid chloride, and then a reducing agent according to a "one-pot" technique:

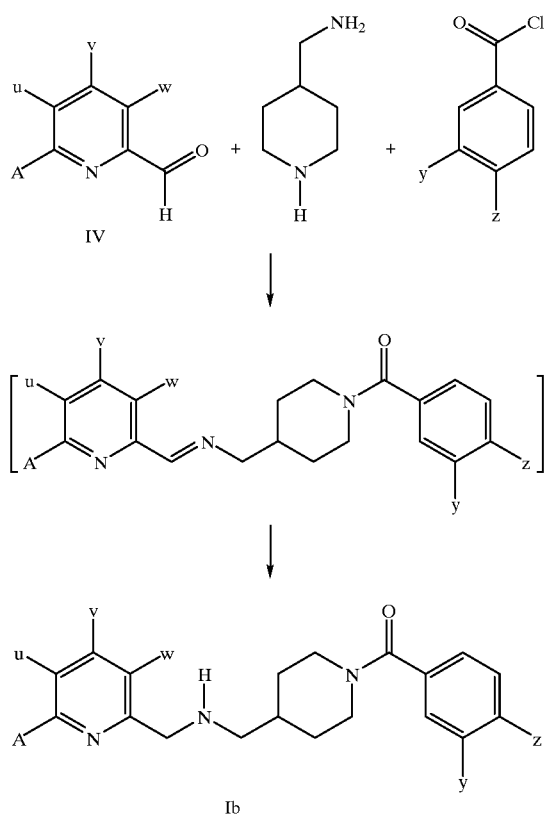

wherein: A, u, v, w, y and z are as defined in claim 1.

6. Process for preparing compound (Ic), wherein (HA) or (A⁻Na⁺) is reacted with a compound of formula (Ia),

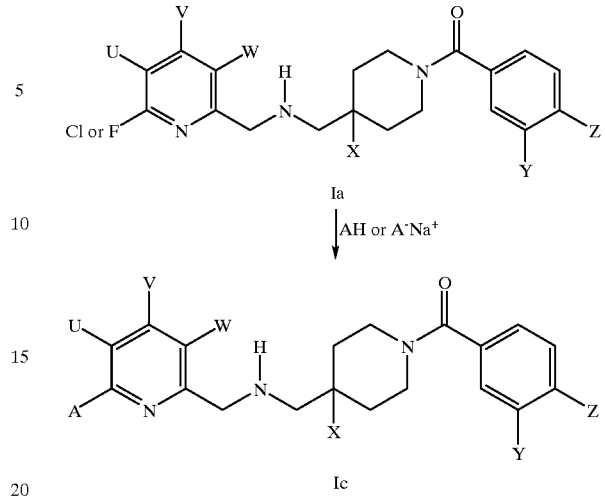

wherein
u, v, w, x, y and z are as defined in claim 1,
A is selected from an amino group or a saturated cyclic amino group or a pyrrol-1-yl, pyrazol-1-yl, imidazol-1-yl or [1,2,4]triazol-1-yl radical.

7. A new synthetic intermediate of formula (V) useful for the preparation of a compound of formula (I):

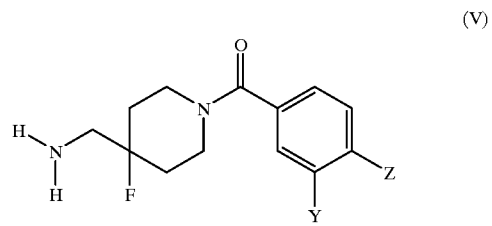

where y and z are as defined in claim 1.

8. A new synthetic intermediate of formula (VI) useful for the preparation of a compound of formula (I):

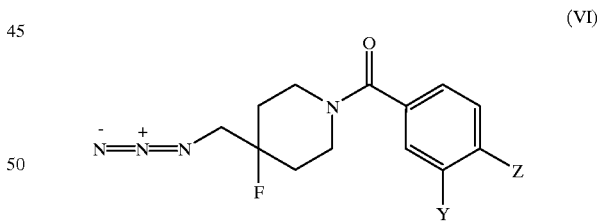

where y and z are as defined in claim 1.

9. Pharmaceutical composition, which comprises, as active ingredient, at least one compound according to claim 1, in combination with one or more pharmaceutically-acceptable excipients or vehicles.

10. Pharmaceutical composition which comprises, as active ingredient, at least one compound according to claim 2, in combination with one or more pharmaceutically-acceptable excipients or vehicles.

11. A method for the treatment of depression, anxiety, aggression, sleeping disorders, high blood pressure, or migraine, in a patient in need thereof, comprising the step of administering to the said patient an effective amount of a compound of claim 1.

12. A method for the treatment of depression, anxiety, aggression, sleeping disorders, high blood pressure, or migraine, in a patient in need thereof, comprising the step of administering to the said patient an effective amount of a compound of claim 2.

13. A compound of claim 1 wherein the saturated aliphatic hydrocarbon radical is selected from the group consisting of methyl, ethyl, propyl, butyl, pentyl, isopropyl, 1-methyl-ethyl, 1-methyl-propyl, 1-methyl-butyl, 2-methyl-propyl, 2-methyl-butyl, 3-methyl-butyl, 1-ethyl-propyl, and 2-ethyl-propyl.

14. A compound of claim 1 wherein the fluoroalkyl radical is selected from the group consisting of monofluoromethyl (—CH$_2$F), difluoromethyl (—CHF$_2$), trifluoromethyl (—CF$_3$), 1-fluoro-1-ethyl (—CHFCH$_3$), and 1,1-difluoro-1-ethyl (—CF$_2$CH$_3$).

15. A compound of claim 1 wherein alkoxycarbonyl is selected from the group consisting of methoxycarbonyl (CH$_3$OCO—) and ethoxycarbonyl (CH$_3$CH$_2$OCO—).

* * * * *

UNITED STATES PATENT AND TRADEMARK OFFICE
CERTIFICATE OF CORRECTION

PATENT NO. : 6,020,345
DATED : February 1, 2000
INVENTOR(S) : Bernard Vacher; Bernard Bonnaud; Wouter Koek Page 1 of 3

It is certified that error appears in the above-indentified patent and that said Letters Patent is hereby corrected as shown below:

Column 3, line 49: "HTLA" should read -- $HT_{1A}$ --.
    Page 5, line 12

Column 30, line 51: "metachloroperbenzoic" should read -- metachloroperbenzoic --. Page 44, line 4

Column 36, line 9: Delete the following from this line: "Error! Undefined marker." Page 54, line 5

Column 43, line 12: Delete "7" at the end of the line.

Column 43, line 13: Insert at the beginning of the line: -- 7. --. Page 66, line 34

Column 47, line 48 (approx.): Delete "{" at the end of the line. Page 73, line 23

Column 47, line 49: Insert -- { -- at the beginning of the line. Page 73, line 23

Column 61, line 54: "N(CCH$_3$).CH:CHCH:C-)," should read: -- N(CH$_3$).CH:CH.CH:C-), -- Page 90, line 16

Column 61, line 55: Delete the word "or" at the end of the line and _insert_ -- , -- (a comma). Page 2 of Preliminary Amendment dtd 5/21/99, Claim 1, (at the top of page 90): lines 12-37:.

Column 61, line 58: "pyrazol-yl," at the beginning of the line, should read: -- pyrazol-1-yl, --.
    Page 90, line 20

UNITED STATES PATENT AND TRADEMARK OFFICE
CERTIFICATE OF CORRECTION

PATENT NO. : 6,020,345
DATED : February 1, 2000
INVENTOR(S) : Bernard Vacher; Bernard Bonnaud; Wouter Koek Page 2 of 3

It is certified that error appears in the above-indentified patent and that said Letters Patent is hereby corrected as shown below:

Column 61, line 59: At the end of the line, "(CH:CH.N:C-)" should read: (CH:CH.NH.N:C-) --. Page 90, line 21

Column 62, line 9: "(CH:CH.S.SN:C-)" should read: -- (CH:CH.S.N:C-) --. Page 91, line 1

Column 62, line 14: At the end of the line, insert a -- . -- (period) after ($CH_3$). Page 91, line 6

Column 62, line 15: At the beginning of the line, delete the "." (period). Page 91, line 6

Column 62, line 17: "($R_1O$)" should read -- ($R_1O$-) --. Page 91, line 8

Column 62, line 31: Insert a "," (comma) after the word "above". Page 2 of Preliminary Amendment dtd 5/21/99, Claim 1, on page 91, line 19.

Column 62, line 42: Insert the word -- or -- at the end of the line. Page 2 of Preliminary Amendment dtd 5/21/99, Claim 1, page 91, line 13.

Column 62, line 45: Delete the first occurrence "acid". Page 2 of Preliminary Amendment dtd 5/21/99, Claim 1, page 91, line 29.

Column 62, line 46: Insert -- claim 1, selected from -- between the words "of" and "the". Page 91, claim 2, line 2.

UNITED STATES PATENT AND TRADEMARK OFFICE
CERTIFICATE OF CORRECTION

PATENT NO. : 6,020,345
DATED : February 1, 2000
INVENTOR(S) : Bernard Vacher; Bernard Bonnaud; Wouter Koek It is certified that error appears in the above-identified patent and that said Letters Patent is hereby corrected as shown below:

Column 62, line 63: Delete the 3rd occurrence "(".
    Page 92, line 14

Column 63, line 2: Insert a -- , -- (comma) at the end of the line. Page 3 of Preliminary Amendment dtd 5/21/99, <u>Claim 2 on page 92, line 20</u>.

Column 63, line 24: At the beginning of the line, "(4-{[6-Azetidin" should read -- (4-{[(6-Azetidin --
    Page 93, line 1

Column 64, line 27: At the end of the line, <u>insert</u> a -- , -- (comma), after the word "ester". Page 3 of Preliminary Amendment dtd 5/21/99, <u>Claim 2 on page 94, line 27</u>.

Column 64, line 56: "-([4-fluoro-" should read:
-- -[4-fluoro- --. Page 95, line 16

Column 65, line 24: "4-fluoro-4-({[(5-" should read:
-- 4-fluoro-4-{[(5- --. Page 96, line 13

Column 68, line 23(approx): At the end of the line, insert the word -- and, --. Page 3 of Preliminary Amendment dtd 5/21/99, <u>Claim 6, on page 100, line 4</u>.

Signed and Sealed this

Thirtieth Day of January, 2001

Attest:

Q. TODD DICKINSON

Attesting Officer      Director of Patents and Trademarks